(12) United States Patent
Link

(10) Patent No.: US 11,857,974 B2
(45) Date of Patent: Jan. 2, 2024

(54) METHOD AND SYSTEM FOR THERMALLY CONTROLLING A CHEMICAL REACTION IN DROPLETS

(71) Applicant: Bio-Rad Laboratories, Inc., Hercules, CA (US)

(72) Inventor: Darren R. Link, Lafayette, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 68 days.

(21) Appl. No.: 17/211,594

(22) Filed: Mar. 24, 2021

(65) Prior Publication Data
US 2021/0299670 A1   Sep. 30, 2021

Related U.S. Application Data

(60) Provisional application No. 62/994,218, filed on Mar. 24, 2020.

(51) Int. Cl.
*C12Q 1/686* (2018.01)
*B01L 7/00* (2006.01)
(Continued)

(52) U.S. Cl.
CPC .......... *B01L 7/5255* (2013.01); *B01L 3/0241* (2013.01); *C12Q 1/686* (2013.01); *G01N 21/6428* (2013.01); *B01L 2300/08* (2013.01); *B01L 2300/18* (2013.01); *B01L 2400/021* (2013.01); *B01L 2400/0409* (2013.01); *G01N 2021/6432* (2013.01); *G01N 2021/6439* (2013.01)

(58) Field of Classification Search
CPC .......... B01L 7/5255; B01L 2200/0673; B01L 2400/0457; B01L 2300/08; B01L 2300/18; B01L 3/0241; B01L 2200/147; B01L 2300/0883; C12Q 1/686
See application file for complete search history.

(56) References Cited

U.S. PATENT DOCUMENTS 9,266,104 B2    2/2016 Link
9,556,470 B2    1/2017 Link et al.
(Continued)

FOREIGN PATENT DOCUMENTS

WO    2010036352 A1    4/2010

OTHER PUBLICATIONS

Ahrberg et al., "Polymerase chain reaction in microfluidic devices," Lab Chip, vol. 16, pp. 3866-3884. (Year: 2016).*
(Continued)

*Primary Examiner* — Young J Kim
(74) *Attorney, Agent, or Firm* — Kolisch Hartwell, P.C.

(57) ABSTRACT

Methods and systems for thermally controlling a chemical reaction in droplets. In an exemplary method, a first thermal zone and a second thermal zone having different temperatures from one another may be created in a reaction chamber. An emulsion including droplets encapsulated by a carrier fluid may be held in the reaction chamber. The droplets may have a density mismatch with the carrier fluid, and each droplet may include one or more reactants for the chemical reaction. An orientation of the reaction chamber may be changed to move the droplets from the first thermal zone to the second thermal zone, such that a rate of the chemical reaction changes in at least a subset of the droplets.

16 Claims, 16 Drawing Sheets

(51) Int. Cl.
*B01L 3/02* (2006.01)
*G01N 21/64* (2006.01)

(56) References Cited

U.S. PATENT DOCUMENTS

| | | |
|---|---|---|
| 2005/0227264 A1 | 10/2005 | Nobile et al. |
| 2014/0051087 A1 | 2/2014 | Makrigiorgos |
| 2015/0152480 A1* | 6/2015 | Idegami .................. C12N 9/96 435/289.1 |
| 2015/0314294 A1 | 11/2015 | Schultz et al. |

OTHER PUBLICATIONS

Cao, Lei, et al. "Advances in digital polymerase chain reaction (dPCR) and its emerging biomedical applications." Biosensors and Bioelectronics 90 (published 2017): pp. 459-474.

The U.S. Receiving Office of WIPO, Written Opinion of the International Searching Authority regarding PCT Application No. PCT/US2021/024015, dated Jun. 4, 2021, 11 pages.

The U.S. Receiving Office of WIPO, International Search Report of the International Searching Authority regarding PCT/US2021/024015, dated Jun. 4, 2021, 2 pages.

* cited by examiner

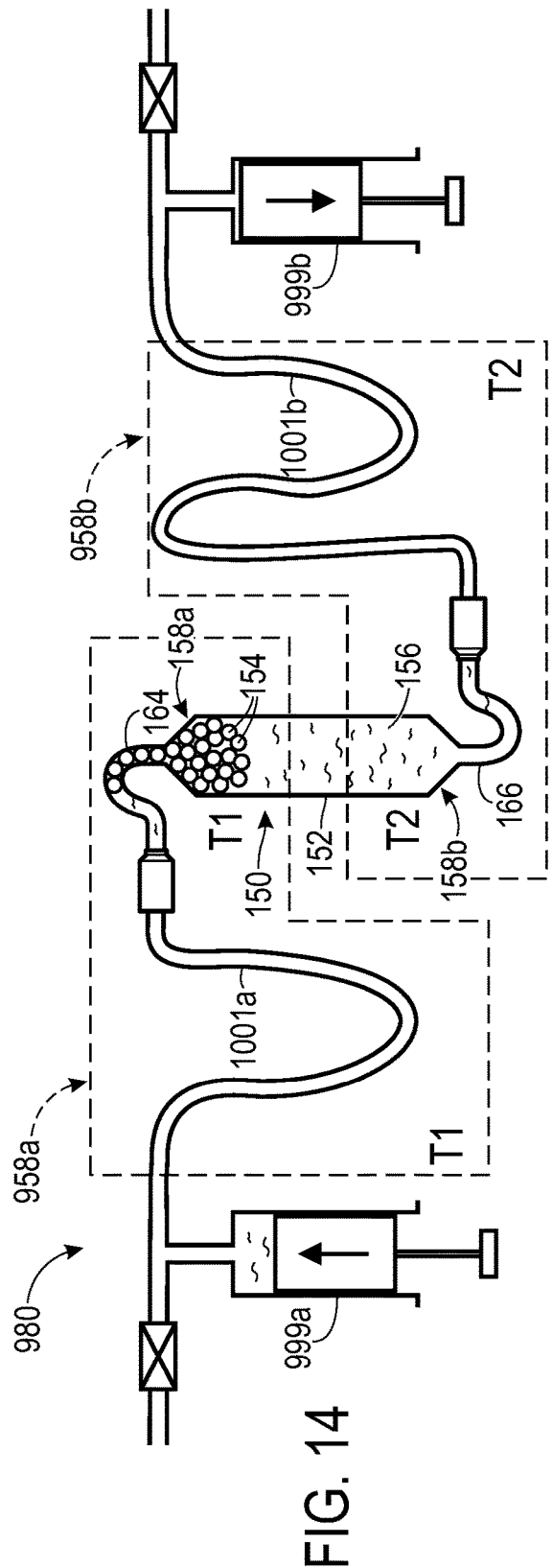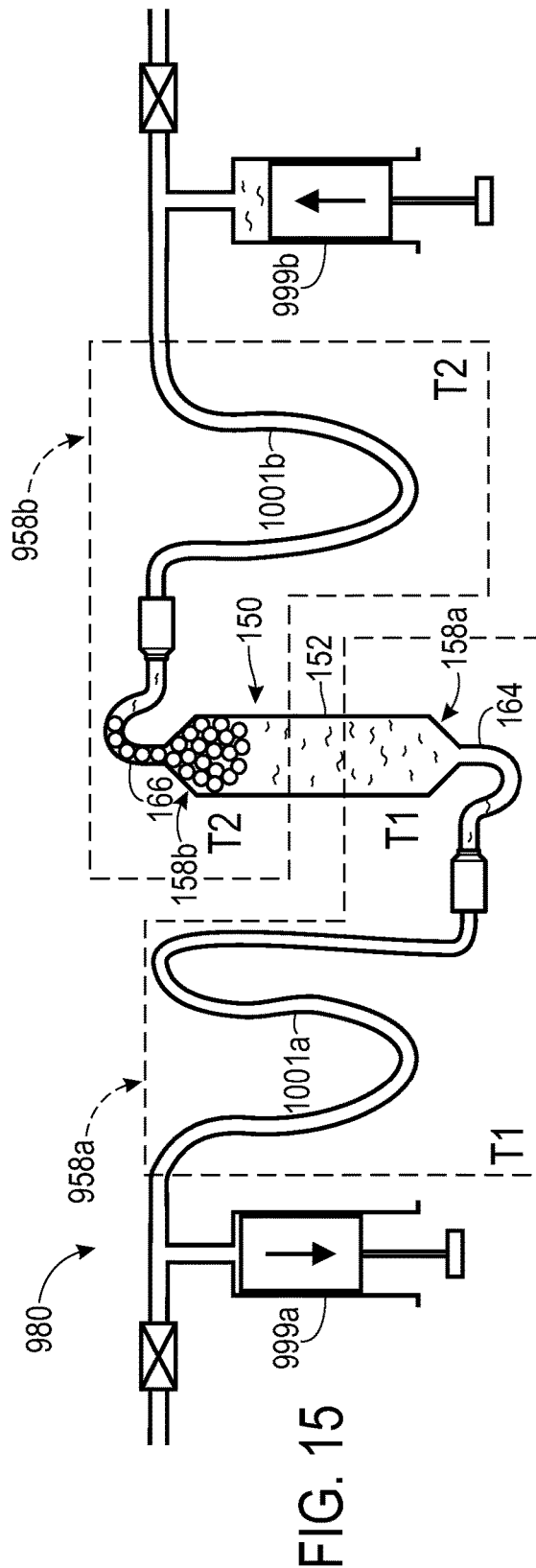

US 11,857,974 B2

METHOD AND SYSTEM FOR THERMALLY CONTROLLING A CHEMICAL REACTION IN DROPLETS

CROSS-REFERENCE TO PRIORITY APPLICATION

This application is based upon and claims the benefit under 35 U.S.C. § 119(e) of U.S. Provisional Patent Application Ser. No. 62/994,218, filed Mar. 24, 2020, which is incorporated herein by reference in its entirety for all purposes.

INTRODUCTION

Nucleic acid amplification by the polymerase chain reaction (PCR) can be performed advantageously in aqueous droplets of an emulsion, with each aqueous droplet forming a separate microreactor. To drive amplification the emulsion is thermally cycled. This thermal cycling can be performed with a standard thermocycler utilizing a design format in which the emulsion is kept stationary and the temperature of the surrounding reaction chamber is cycled between different temperatures. However, cycling the temperature of the entire reaction chamber is slow, which produces long cycling times and lowers throughput.

FIG. 1 shows a thermocycling device 30 to speed up the thermal cycling of droplets (see U.S. Pat. No. 9,266,104). Thermocycling device 30 has a reaction chamber 32 for holding an emulsion 33 including droplets 34 suspended in an immiscible carrier fluid 36. An inlet channel 38 conducts preheated carrier fluid of different selected temperatures into reaction chamber 32, indicated by an inflow arrow at 40. At the same time, an outlet channel 42 conducts a matching volume of carrier fluid 36 out of reaction chamber 32, indicated by an outflow arrow at 44. Droplets 34 remain in reaction chamber 32 and are heated/cooled to each of the different selected temperatures by the incoming preheated carrier fluid. In this manner, thermocycling device 30 can thermally cycle droplets 34 rapidly in reaction chamber 32 to amplify a target sequence contained by the droplets. However, cyclically delivering carrier fluid of different temperatures to the reaction chamber consumes a significant volume of the carrier fluid, and the speed and precision of each temperature change are sensitive to the thermal mass of the reaction chamber and its contents. A different approach for thermally controlling amplification and other chemical reactions is needed.

SUMMARY

The present disclosure provides methods and systems for thermally controlling a chemical reaction in droplets. In an exemplary method, a first thermal zone and a second thermal zone having different temperatures from one another may be created in a reaction chamber. An emulsion including droplets encapsulated by a carrier fluid may be held in the reaction chamber. The droplets may have a density mismatch with the carrier fluid and each droplet may include one or more reactants for the chemical reaction. An orientation of the reaction chamber may be changed to move the droplets from the first thermal zone to the second thermal zone, such that a rate of the chemical reaction changes in at least a subset of the droplets.

BRIEF DESCRIPTION OF THE DRAWINGS

FIG. 14 is a schematic fragmentary illustration of selected aspects of an exemplary system for thermally controlling a chemical reaction in droplets and including a pair of pumps to drive preheated carrier fluid into respective thermal zones of a reaction chamber holding the droplets.

FIG. 15 is another view of the system of FIG. 14 taken after the reaction chamber has been reoriented to move the droplets between the thermal zones within the reaction chamber.

DETAILED DESCRIPTION

Figure 1:
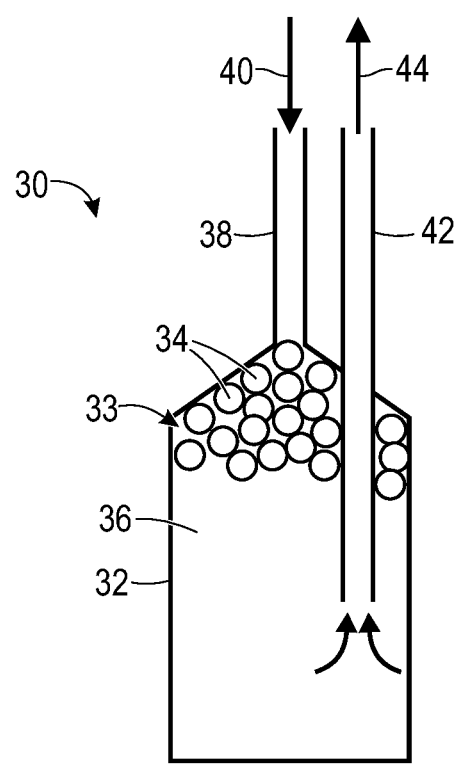
FIG. 1 is a schematic fragmentary view of a thermocycling device illustrating a prior art approach to thermally cycling droplets in a reaction chamber by cyclical flow of preheated carrier fluid of different temperatures into the reaction chamber.

The present disclosure provides methods and systems for thermally controlling a chemical reaction in droplets. In an exemplary method, a first thermal zone and a second thermal zone having different temperatures from one another may be created in a reaction chamber. An emulsion including droplets encapsulated by a carrier fluid may be held in the reaction chamber. The droplets may have a density mismatch with the carrier fluid, and each droplet may include one or more reactants for the chemical reaction. An orientation of the reaction chamber may be changed to move the droplets from the first thermal zone to the second thermal zone, such that a rate of the chemical reaction changes in at least a subset of the droplets. The methods and systems described herein offer various advantages, such as greater simplicity, more rapid and precise thermal control of chemical reactions, faster thermal cycling, and/or the like.

Further aspects of the present disclosure are described in the following sections: (I) definitions, (II) overview of the methods and systems, (III) examples, and (IV) selected aspects.

I. DEFINITIONS

Technical terms used in this disclosure have meanings that are commonly recognized by those skilled in the art. However, the following terms may be further defined as follows.

Amplicon—a product of an amplification reaction.

Amplification—a process whereby multiple copies are made of an amplicon matching and/or complementary to a target sequence. The process interchangeably may be called an amplification reaction. Amplification may, for example, generate an exponential or linear increase in the number of copies as amplification proceeds. Typical amplifications may produce a greater than 1,000-fold increase in the number of copies of an amplicon. Exemplary amplification reactions for the methods disclosed herein may include a polymerase chain reaction (PCR) or a ligase chain reaction (LCR), each of which is driven by thermal cycling (e.g., 2-step, 3-step, or >3-step thermal cycling). The methods also or alternatively may use other amplification reactions, which may be performed isothermally, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and/or the like. Amplification may utilize a linear or circular template.

Amplification reagents—any reagents that promote or affect amplification of a target sequence. The reagents may include any combination of at least one primer or primer pair for amplification of at least one target sequence, at least one label for detecting amplification of the at least one target sequence (e.g., at least one probe including a label and/or a DNA intercalating dye as a label), at least one polymerase enzyme and/or ligase enzyme (which may be heat-stable), and nucleoside triphosphates (dNTPs and/or NTPs), among others.

Analyte—a chemical substance or region thereof that is the subject of an analysis to detect, quantify, and/or characterize the chemical substance or region thereof. Exemplary analytes include a reactant, catalyst, cofactor, or the like, for a chemical reaction. Suitable analytes may include nucleic acids, nucleic acid target sequences, proteins (e.g., enzymes), carbohydrates, lipids, and the like.

Chemical reaction—a process that involves rearrangement of the molecular or ionic structure of one or more substances. Each of the substances is referred to as "reactant" for the chemical reaction. A chemical reaction may be unimolecular (only one chemical reactant that reacts with itself), bimolecular (two chemical reactants that react with one another), trimolecular (three chemical reactants that react with one another), etc. Exemplary classes of chemical reactions that may be suitable include oxidation-reduction, direct combination, decomposition, single displacement/substitution, double displacement/substitution, acid-base, isomerization, racemization, ring opening, cyclization, and hydrolysis reactions, among others. The chemical reaction may or may not be performed in the presence of an enzyme that catalyzes the chemical reaction.

Complementary—related by the rules of base pairing. A first nucleic acid, or region thereof, is "complementary" to a second nucleic acid if the first nucleic acid or region is capable of hybridizing with the second nucleic acid in an antiparallel fashion by forming a consecutive or nearly consecutive series of base pairs. The first nucleic acid (or region thereof) is termed "perfectly complementary" to the second nucleic acid if hybridization of the first nucleic acid (or region thereof) to the second nucleic acid forms a consecutive series of base pairs using every nucleotide of the first nucleic acid or region thereof. A "complement" of a first nucleic acid is a second nucleic acid that is perfectly complementary to the first nucleic acid for at least ten consecutive nucleotides. The "complementarity" between a first nucleic acid (or region thereof) and a second nucleic acid (or region thereof) refers to the number or percentage of base pairs that can be formed when the first nucleic acid (or region thereof) is optimally aligned for hybridization in an antiparallel fashion with the second nucleic acid (or region thereof). A first nucleic acid or region thereof that is complementary to a second nucleic acid or region thereof generally has a complementarity of at least 80% or 90%.

Droplet—a small volume of liquid encapsulated by an immiscible fluid (e.g., encapsulated by an immiscible liquid, which may form a continuous phase of an emulsion). The immiscible liquid may include oil and/or may be composed predominantly of oil. Droplets for the methods disclosed herein may, for example, have an average size of less than about 1 µL, 500 nL, 100 nL, 10 nL, or 1 nL, among others. The droplets may, for example, be aqueous droplets.

Inversion—reorientation of greater than 90 degrees and less than 270 degrees with respect to a vertical axis (defined by gravity) or with respect to a g-force vector. The verb "invert" refers to the process of producing this reorientation.

Label—an identifying and/or distinguishing marker or identifier associated with a structure, such as a primer, probe, amplicon, droplet, or the like. The label may be associated covalently with the structure, such as a label that is covalently attached to an oligonucleotide, or associated non-covalently (e.g., by intercalation, hydrogen bonding, electrostatic interaction, encapsulation, etc.). Exemplary labels include optical labels, radioactive labels, magnetic labels, electrical labels, epitopes, enzymes, antibodies, etc. Optical labels are detectable optically via their interaction with light. Exemplary optical labels that may be suitable include photoluminophores, quenchers, and intercalating dyes, among others.

Light—optical radiation including ultraviolet light, visible light, and/or infrared light.

Nucleic acid—a polymer of any length composed of naturally-occurring nucleotides (e.g., where the polymer is DNA or RNA), or a substance produced synthetically that can hybridize with DNA or RNA in a sequence-specific manner analogous to that of two naturally occurring nucleic acids, e.g., can participate in Watson-Crick base pairing interactions. A nucleic acid may be composed of any suitable number of nucleotides, such as at least about 5, 10, 100, or 1000, among others. Generally, the length of a nucleic acid corresponds to its source, with synthetic nucleic acids (e.g., oligonucleotides) typically being shorter, and biologically/enzymatically generated nucleic acids (e.g., genomic fragments) typically being longer.

A nucleic acid may have a natural or artificial structure, or a combination thereof. Nucleic acids with a natural structure, namely, deoxyribonucleic acid (DNA) and ribonucleic acid (RNA), generally have a backbone of alternating pentose sugar groups and phosphate groups. Each pentose group is linked to a nucleobase (e.g., a purine (such as adenine (A) or guanine (G)) or a pyrimidine (such as cytosine (C), thymine (T), or uracil (U))). Nucleic acids with an artificial structure are analogs of natural nucleic acids and may, for example, be created by changes to the pentose and/or phosphate groups of the natural backbone and/or to one or more nucleobases. Exemplary artificial nucleic acids include glycol nucleic acids (GNAs), peptide nucleic acids (PNAs), locked nucleic acids (LNAs), threose nucleic acids (TNAs), xeno nucleic acids (XNA), and the like.

The sequence of a nucleic acid is defined by the order in which nucleobases are arranged along the backbone. This sequence generally determines the ability of the nucleic acid to hybridize with another nucleic acid by hydrogen bonding. In particular, adenine pairs with thymine (or uracil) and guanine pairs with cytosine.

Oligonucleotide—a relatively short and/or chemically synthesized nucleic acid. The length of an oligonucleotide may, for example, be 3 to 1000 nucleotides, among others.

Partial occupancy—present in each droplet of only a subset of droplets. An analyte at partial occupancy within a set of droplets refers to a configuration in which one or more of the droplets each contains no copy of the analyte and one or more of the droplets each contains at least one copy of the analyte. In some cases, one or more of the droplets each contains exactly one copy of the analyte. The analyte may or may not have a Poisson distribution among the droplets.

Photoluminescence—emission of light induced by electromagnetic radiation. Photoluminescence may be produced by any form of matter in response to absorption of photons of electromagnetic radiation, such as light. Exemplary forms of photoluminescence include fluorescence and phosphorescence, among others.

Primer—an oligonucleotide capable of serving as a point of initiation of template-directed nucleic acid synthesis under appropriate reaction conditions (e.g., in the presence of a template to which the oligonucleotide anneals, nucleoside triphosphates, and a polymerization catalyst (such as a DNA or RNA polymerase or a reverse transcriptase), in an appropriate buffer and at a suitable temperature). The primer may have any suitable length, such as 5 to 500 nucleotides, among others. The primer may be a member of a "primer pair" including a "forward primer" and a "reverse primer" that define the ends of an amplicon generated in an amplification reaction. (The adjectives "forward" and "reverse" are arbitrary designations relative to one another.) The forward primer hybridizes with a complement of the 5'-end region of a target sequence to be amplified, and the reverse primer hybridizes with the 3'-end region of the target sequence. The term "primer binding site" refers to a portion of a template (or its complement) to which a primer anneals. The full sequence of the primer need not be perfectly complementary to the primer binding site, just sufficiently complementary to anneal under the conditions of the reaction. Accordingly, the primer may have a 3'-end region that is complementary to the primer binding site, and a 5'-end region that is not complementary to the primer binding site (and forms a "5'-tail").

Probe—a labeled oligonucleotide configured to report the occurrence of an amplification reaction and/or formation of an amplicon by the amplification reaction. A probe may, for example, be a photoluminescent probe including an oligonucleotide labeled with a photoluminophore. A probe may be configured to hybridize with at least a portion of an amplicon generated by amplification. The probe (e.g., a hydrolysis probe) may be configured to hybridize with at least a portion of an amplicon during an annealing/extension phase of amplification cycles of an amplification reaction, or the probe (e.g., a molecular beacon probe) may be configured to hybridize with the amplicon after the amplification reaction has been completed, among others.

Reaction chamber—a substantially or completely enclosed space inside a container for performing a chemical reaction. A reaction chamber may or may not include one or more channels and/or distinct subchambers. The reaction chamber may be designed to hold an emulsion and particularly droplets thereof and retain the droplets in the reaction chamber while the reaction chamber is being reoriented to control a chemical reaction in the droplets. The reaction chamber may or may not be elongated between a pair of opposite ends, and may or may not have a uniform cross section or diameter intermediate the opposite ends. In some cases, it may be preferable to have a non-uniform reaction chamber with a larger volume at opposite ends and a smaller volume intermediate the opposite ends. This configuration allows the separation distance between the opposite ends to be increased to better maintain the temperature difference between the opposite ends. The reaction chamber may or may not be axially symmetric. In some cases, the reaction chamber may be or include a channel of elliptical (e.g., circular) or polygonal (e.g., rectangular) cross-section. The reaction chamber may be formed by, and/or cladded with, one or more metals or plastics that are machined, molded, fused, brazed, or the like. In some cases, it may be advantageous to use a combination of high thermal conductivity and low thermal conductivity materials, to encourage conduction of heat within each thermal zone while discouraging conduction of heat between thermal zones.

Sensed zone—a space from which a reaction signal is detected. The term "reaction signal" refers to any detectable signal that is sensitive to the occurrence of a chemical reaction in droplets.

Target sequence—a sequence of or within a template providing a pattern for synthesis of a complementary sequence.

Template—a nucleic acid that serves as a pattern for synthesis of a complementary strand. The template may provide a primer binding site for a primer, which is extended by sequential addition of complementary nucleotides according to the pattern.

Thermal zone—an area having a controlled temperature, such as a temperature actively maintained at a selected set point. The area may be only a portion of the space defined by a reaction chamber. A thermal zone may include an end or recess of the reaction chamber at which droplets can accumulate when the reaction chamber is reoriented.

II. OVERVIEW OF THE METHODS AND SYSTEMS

This section provides an overview of the methods and systems of the present disclosure for thermally controlling a chemical reaction in droplets; see FIGS. 2-5.

Figure 2:
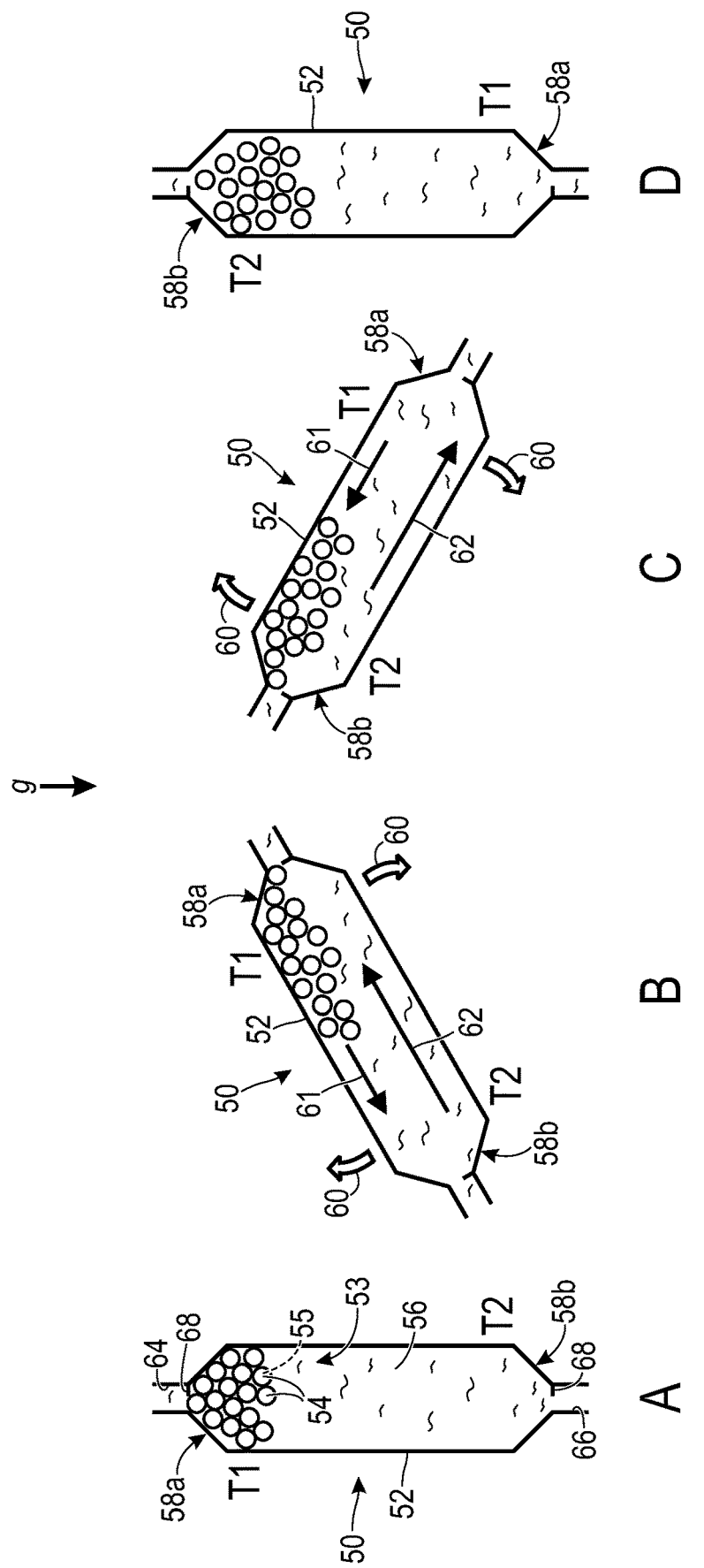
FIG. 2 is a schematic fragmentary illustration, in a series of panels (A-D), of selected aspects of an exemplary reaction control device being used to change the temperature of droplets to control a chemical reaction within the droplets, by changing the orientation of a reaction chamber holding the droplets, with respect to a gravity or g-force vector, to move the droplets between a pair of thermal zones within the reaction chamber.

FIG. 2 shows an exemplary reaction control device 50 having a reaction chamber 52 to hold an emulsion 53. The emulsion includes droplets 54 containing reactants 55 for a chemical reaction (see panel A). Each droplet 54 is encapsulated by an immiscible carrier fluid 56 (a liquid) and has a different density than the carrier fluid. (The droplets may have the same density as one another.) This density mismatch between the droplets and the carrier fluid causes the droplets to either move to the top of reaction chamber 52 (i.e., if the droplets are less dense than the carrier fluid) or to the bottom of reaction chamber 52 (i.e., if the droplets are denser than the carrier fluid). For consistency, in each of the depicted embodiments of the present disclosure, the droplets have a lower density than the carrier fluid and thus are buoyant in the carrier fluid.

The direction of the force of gravity, g, for panels A-D is indicated with an arrow at the top center of FIG. 2 and is opposite the buoyant force that urges droplets 54 toward the top of reaction chamber 52. In other embodiments, each droplet 54 has a higher density than carrier fluid 56 and is urged downward in reaction chamber 52 by gravity. In some examples, a g-force larger than gravity may be applied to reaction chamber 52 by centrifugation, to increase the buoyant (or sedimenting) force on the droplets, thereby driving faster travel of droplets within the reaction chamber (see Example 5).

Reaction control device 50 is configured to create two or more thermal zones in reaction chamber 52. Here, a pair of thermal zones 58a, 58b are created at opposite ends of reaction chamber 52 and have different temperatures, T1 and T2, respectively. In other examples, three or more thermal zones are created having three or more different temperatures (see Example 3).

Panels A-D illustrate changing the orientation of reaction chamber 52, indicated by turning arrows at 60, to move droplets 54 as a group from thermal zone 58a to thermal zone 58b. More specifically, the orientation of reaction chamber 52 is changed with respect to the direction of gravity (and/or an additional g-force) to encourage the desired migration of droplets 54. In the depicted embodiment, reaction chamber 52 is inverted to produce this migration. Thermal zone 58a is at the top of reaction chamber 52 in panel A, while thermal zone 58b has this position in panel D. Accordingly, droplets 54 have temperature T1 in panel A and temperature T2 in panel D. T2 can be less than T1, such that reorientation cools the droplets (i.e., lowers their temperature), which may slow or stop (or start or speed up) the chemical reaction with reactants 55 in the droplets (i.e., in at least a subset (one or more) of the droplets). Alternatively, T2 can be greater than T1, such that reorientation heats the droplets (i.e., raises their temperature), which may start or speed up (or slow or stop) the chemical reaction in the droplets (i.e., in at least a subset (one or more) of the droplets).

Once reorientation is completed, rotation of reaction chamber 52 may be paused for any suitable dwell time, to permit incubation of the droplets at temperature T2 in thermal zone 58b. If desired, reaction chamber 52 then may be reoriented further, such as to move droplets 54 back to thermal zone 58a (or to a third thermal zone within the reaction chamber). When this process is used to thermally cycle the droplets, the cycle number, each temperature, and the dwell time of the droplets at each temperature are readily controlled.

Movement of droplets 54 toward thermal zone 58b, as reaction chamber 52 is being reoriented, is indicated with a motion arrow 61 in panels B and C. This movement is accompanied by a net flow of carrier fluid 56 that is displaced by droplets 54, indicated by a flow arrow at 62, in the opposite direction toward thermal zone 58a.

Droplets 54 and carrier fluid 56 can enter and leave reaction chamber 52, at the appropriate times, via one or more ports, such as an inlet 64 and an outlet 66. In some examples, inlet 64 may function as both an inlet and an outlet for the emulsion, and outlet 66 may function only as a vent. An upstream valve and a downstream valve may be operatively connected to inlet 64 and outlet 66, respectively, to control when fluid flow through either or both the inlet and the outlet is permitted. In some examples, both valves may remain closed while emulsion 53 is being processed in reaction chamber 52 (e.g., when reaction chamber 52 is being reoriented). In some examples, both valves may be opened to allow preheated carrier fluid to be added to reaction chamber 52 during processing of emulsion 53 (e.g., see Example 4).

Reaction control device 50 may have a respective gate 68 associated with each port to limit travel of droplets 54 out of reaction chamber 52. Gate 68 may, for example, be a structure that passively blocks travel of droplets 54 out of reaction chamber 52 until a sufficient pressure differential is created with a pump to force the droplets past the gate.

Figure 3:
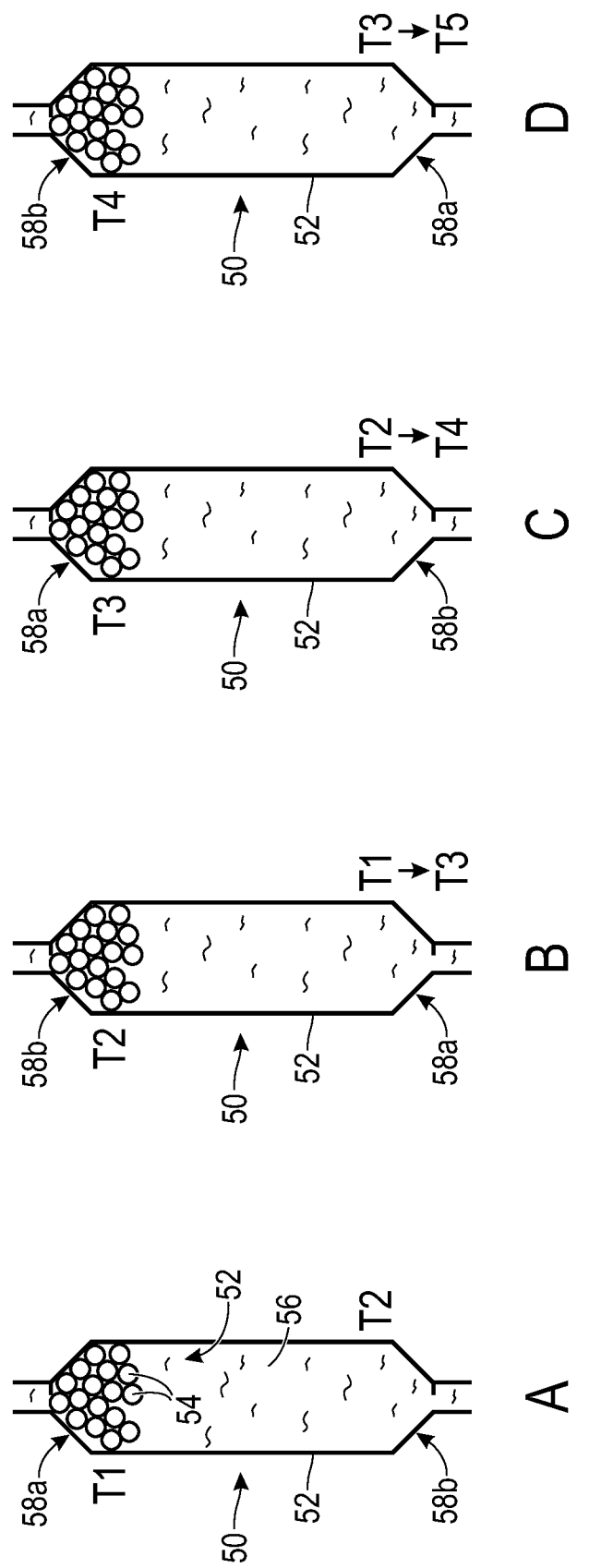
FIG. 3 is a schematic fragmentary illustration, in a series of panels (A-D), of the reaction control device of FIG. 2 being used to expose droplets to a series of different temperatures by changing the temperature of each thermal zone of the reaction chamber.

FIG. 3 shows reaction control device 50 being used to expose droplets 54 to a series of different temperatures (T1-T5). The different temperatures may, for example, be a series of increasing temperatures or decreasing temperatures, to respectively step up or step down the temperature of the droplets. Stepping up or down the droplet temperature may be used to generate a melting curve or an annealing curve for one or more nucleic acid duplexes in the droplets (e.g., see Example 5). The melting/annealing curve may allow amplification of two or more different target sequences to be distinguished from one another using the same probe and/or label.

Panels A-D illustrate an exemplary series of configurations. In panel A, droplets 54 are located in thermal zone 58a at a temperature of T1. In panel B, reaction chamber 52 has been reoriented to move droplets 54 to thermal zone 58b having temperature T2. While droplets 54 are being incubated in thermal zone 58b, the other thermal zone, 58a, is being changed to temperature T3. In panel C, reaction chamber 52 has been reoriented again to move droplets 54 back to thermal zone 58a, for incubation at T3. While droplets 54 are located in thermal zone 58a, the other thermal zone, 58b, is being changed to temperature T4. In panel D, reaction chamber 52 has been reoriented yet again to move droplets 54 back to thermal zone 58b, for incubation at T4. During this incubation, the other thermal zone, 58a, is being changed to temperature T5 to further extend the temperature series over which the droplets are incubated. In other examples, the temperature of only one of the thermal zones may be changed.

Figure 4:
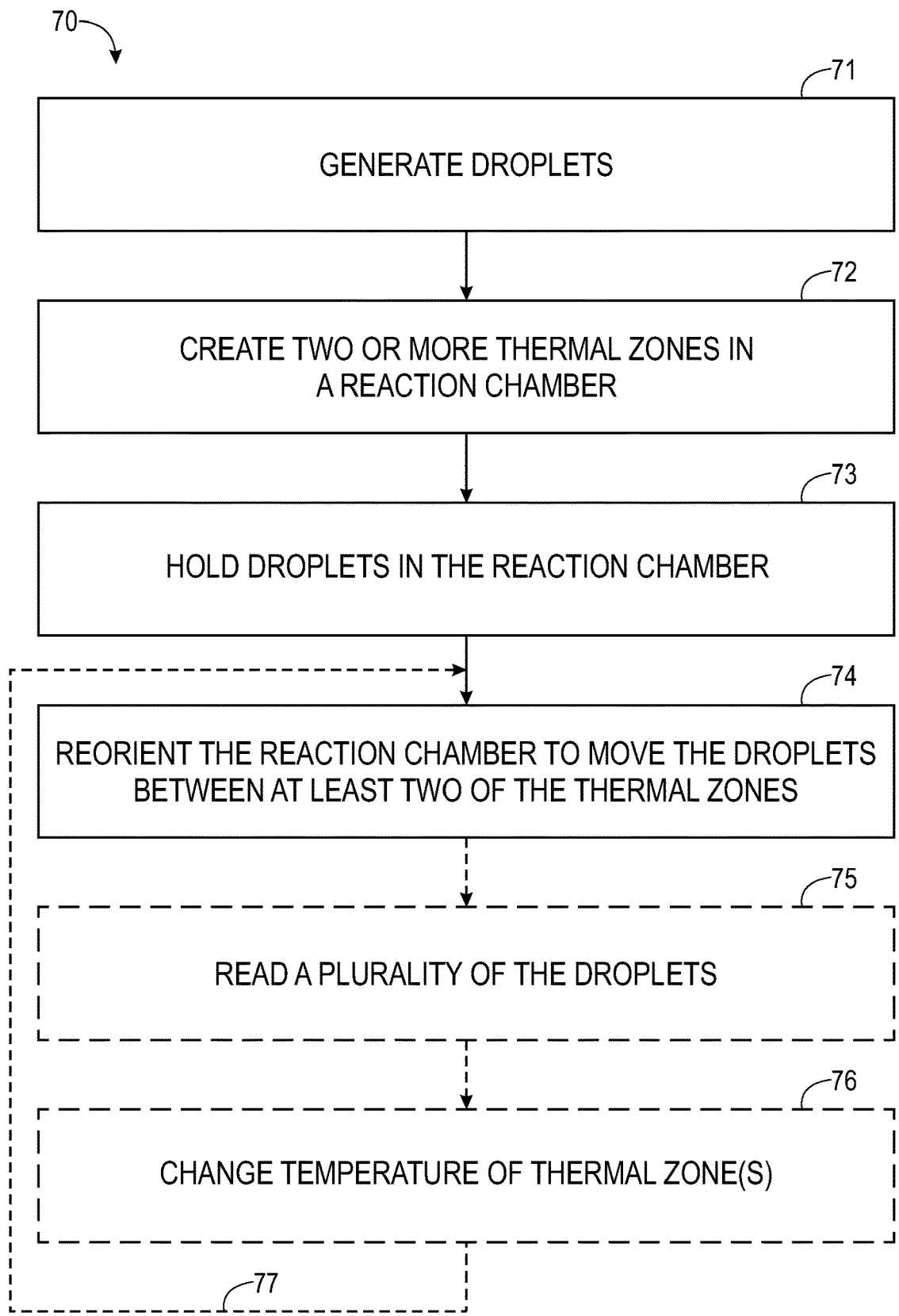
FIG. 4 is a flowchart listing exemplary steps for a method of thermally controlling a chemical reaction in droplets.

FIG. 4 shows a flowchart listing exemplary steps for a method 70 of thermally controlling a chemical reaction in droplets. The steps listed may be performed in any suitable order and combination, and may be modified as described elsewhere herein. The steps shown in dashed boxes and connected by dashed arrows provide exemplary options for modifying the basic method.

Droplets of an emulsion may be generated, indicated at step 71. The droplets may be generated outside the reaction chamber and then introduced into the reaction chamber, or may be generated inside the reaction chamber (e.g., see Examples 5 and 6). Each droplet, or only a subset of the droplets, may contain each reactant required for the chemical reaction. The droplets may be sample-containing droplets each containing a portion of the same sample. The droplets may contain an analyte at partial occupancy, which means that each droplet of only a subset of the droplets contains at least one copy of analyte, and, optionally, each droplet of only a subset of the droplets contains no copies of the analyte. The analyte may, for example, be a nucleic acid, nucleic acid target sequence, protein, carbohydrate, lipid, or the like.

The droplets may be generated by any suitable procedure and/or device. In some examples, the droplets may be generated by dividing a bulk phase mixture, which may contain the reactant(s), the sample, and any other suitable reagents for performing the chemical reaction and/or detecting occurrence of the chemical reaction. In some examples, the droplets may be generated by fusing other droplets with one another.

Two or more thermal zones may be created in a reaction chamber, indicated at 72. The thermal zones may have different, individually selectable and controllable temperatures. Creating the thermal zones may be performed before or after the droplets are present in the reaction chamber. Each thermal zone may represent any suitable portion of the reaction chamber by volume, such as at least about 10%, 20%, 30%, 40%, or 50% of the volume. In some examples, the thermal zones, collectively, may represent more than 50%, 60%, 70%, or 80% of the total volume of the reaction chamber. The temperature of each thermal zone may remain substantially constant until droplet processing is completed, or may be adjusted to a different temperature at any suitable time after the droplets are located in the reaction chamber.

The droplets may be held in the reaction chamber, indicated at 73. Holding the droplets means that the droplets are contained in the reaction chamber, and may be moving, stationary, or a combination thereof, while being held.

The reaction chamber may be reoriented to move the droplets between at least two of the thermal zones, indicated 74. Reorienting the reaction chamber means changing the orientation of the reaction chamber sufficiently with respect to gravity or a g-force, to produce migration of the droplets en masse to a different thermal zone of the reaction chamber. Reorienting may, for example, include turning the reaction chamber at least about one-fourth or one-half turn, or about one full turn, among others (e.g., see Examples 2-5).

A plurality of the droplets may be read, indicated at 75. Reading means collecting reaction data from the plurality of droplets, where the reaction data relates to occurrence of the chemical reaction. The reaction data may be collected by detecting a reaction signal that reflects whether or not the chemical reaction has occurred and/or the extent of occurrence. Detecting a reaction signal may include detecting any suitable type of signal, such as an optical or other electromagnetic signal, an electrical signal, a magnetic signal, radioactive decay, or the like. In some embodiments, the reaction signal may be an amplification signal for an amplification reaction performed in the droplets.

The step of reading may be performed any suitable number of times. In some examples, a plurality of the droplets may be read only once. For example, the droplets may be read inside the reaction chamber (e.g., see Example 5) or removed from the reaction chamber and read outside the reaction chamber (e.g., see Example 6). In other examples, the droplets may be read multiple times, such as inside the reaction chamber, where the temperature of the droplets is changed between each reading (e.g., see Example 5). If performed inside the reaction chamber, reading may be performed on droplets that are moving in response to reorientation of the reaction chamber, such as on droplets passing through a sensed zone of a channel within the reaction chamber.

The temperature of one of more of the thermal zones may be changed, indicated at 76. In other words, the droplets may be exposed serially to two or more different selected temperatures in the same thermal zone. Changing the temperature of a thermal zone permits, for example, a thermal cycling profile to be changed between different thermal cycles of an amplification reaction, or generation of a melting curve or an annealing curve for an amplicon generated in an amplification reaction that includes the chemical reaction.

The reaction chamber may be reoriented multiple times, indicated by a return arrow at 77. For example, the reaction chamber may be reoriented multiple times to thermally cycle the droplets to promote a polymerase chain reaction (PCR) or a ligase chain reaction (LCR), among others. The droplets may be thermally cycled for any suitable number of cycles, such as at least 10, 20, 25, or 30, among others. The thermal cycling may be two-step thermal cycling, in which each cycle has only two temperature steps (e.g., a denaturation temperature and an annealing/extension temperature). In other examples, the thermal cycling may be at least three-step thermal cycling, in which each thermal cycle has three or more temperature steps (e.g., a denaturation temperature, an annealing temperature, and an extension temperature).

Figure 5:
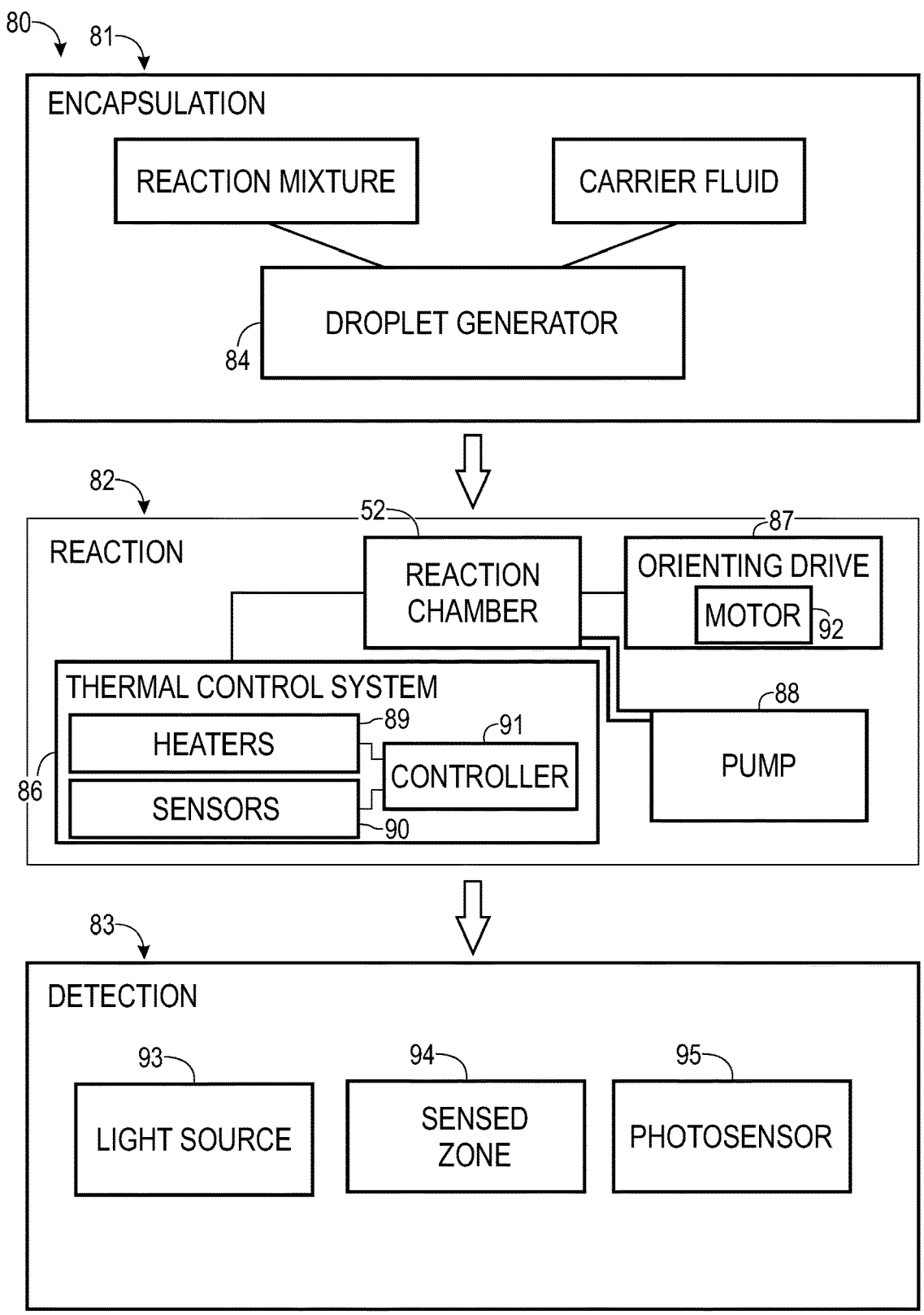
FIG. 5 is a block diagram of an exemplary system for thermally controlling a chemical reaction in droplets.

FIG. 5 shows a block diagram of an exemplary system 80 for thermally controlling a chemical reaction in droplets. System 80 may include an encapsulation portion 81, a reaction portion 82, and a detection portion 83. Here, portions 81-83 are shown as being separate and operating in series (also see Example 6). However, portions 81-83 may have any suitable overlap with one another. For example, encapsulation portion 81 may be incorporated into reaction portion 82 (e.g., see Example 5), and/or detection portion 83 may include a part of reaction portion 82 (e.g., see Example 5).

Encapsulation portion 81 generates droplets of an emulsion. The encapsulation portion may include at least one droplet generator 84. Droplet generator 84 may receive a reaction mixture and a carrier fluid, and form droplets of the reaction mixture surrounded by the carrier fluid. The droplet generator may operate by any suitable mechanism, such as cross-flow, co-flow, flow-focusing, or a confinement gradient, among others. The mechanism may operate in any suitable mode, such as dripping, squeezing, jetting, tip-streaming, tip-multi-breaking, or the like.

Reaction portion 82 includes a reaction chamber 52, which may be operatively connected to a thermal control system 86, an orienting drive 87, a pump(s) 88, and/or a centrifuge (e.g., see Example 5), among others. Reaction portion 82 is exemplified by various reaction control devices disclosed herein, such as in Examples 1-6.

Thermal control system 86 provides temperature control of reaction chamber 52 to create two or more thermal zones therein. The thermal control system may include any suitable number of heaters 89 in thermal communication with each thermal zone of reaction chamber 52. Exemplary heaters (also called heating devices) may be conductive, convective, and/or radiative heaters, and may be located outside (or inside) the reaction chamber. At least one temperature sensor 90 may be operatively associated with each thermal zone of the reaction chamber 52. At least one controller 91 may be in communication with heaters 89 and sensors 90 to form a feedback loop for maintaining the temperature of each thermal zone based on a set point.

Orienting drive 87 is a device operatively connected to reaction chamber 52 and configured to turn reaction chamber 52 with respect to a gravity vector or a g-force vector, to change the orientation of reaction chamber 52. A motor 92 of the orienting drive may generate torque, which may drive rotation of reaction chamber 52 about a rotation axis. Orienting drive 87 may turn reaction chamber 52 in only one rotational direction or in opposite rotational directions, among others.

At least one pump 88 may be operatively connected to reaction chamber 52. Operation of the pump(s) may drive fluid, such as preheated carrier fluid, into and/or out of the reaction chamber. The reaction chamber may be isolated from pump(s) 88 by a valve(s), which may be opened and closed, at any suitable times.

Detection portion 83 may be configured to detect any suitable light from the droplets, such as emitted light, scattered light, polarized light, and/or the like. The light detected may, for example, include luminescence emitted from a luminescent label present in the droplets. The label may be photoluminescent or chemiluminescent, among others. A light source 93 may generate light for irradiating droplets located in a sensed zone 94. The light from light source 93 may propagate to sensed zone 94 via any suitable irradiation optics. Sensed zone 94 may be formed by a channel or a chamber, among others. In some embodiments, sensed zone 94 may be at least a portion of a channel or a chamber that is irradiated by light source 93 and that is optically coupled to at least one photosensor 95. Sensed zone 94 may be located inside or outside reaction chamber 52. Reaction control devices having a sensed zone inside a reaction chamber are described elsewhere herein, such as in Examples 2 and 5.

III. EXAMPLES

This section describes additional aspects and features of methods and systems for thermally controlling a chemical reaction in droplets. Any suitable aspects and features of this section may be combined with one another and with any suitable aspects and features described elsewhere in the present disclosure, such as in Sections I, II, and IV, in any suitable combination. The examples of this section are intended for illustration and should not limit the entire scope of the present disclosure.

Example 1. Droplet-Retention Gates for Reaction Chambers

Figure 6:
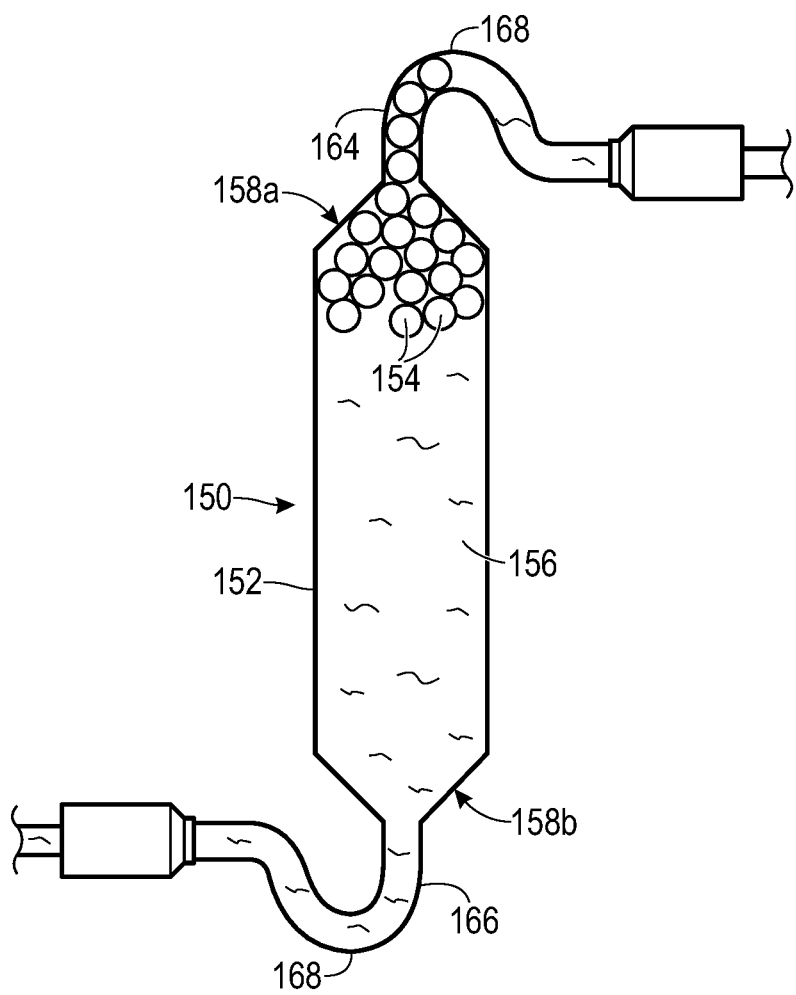
FIG. 6 is a side view of another exemplary reaction chamber holding an emulsion and having curved (swan neck) droplet-retention gates at opposite ends of the reaction chamber.
Figure 7:
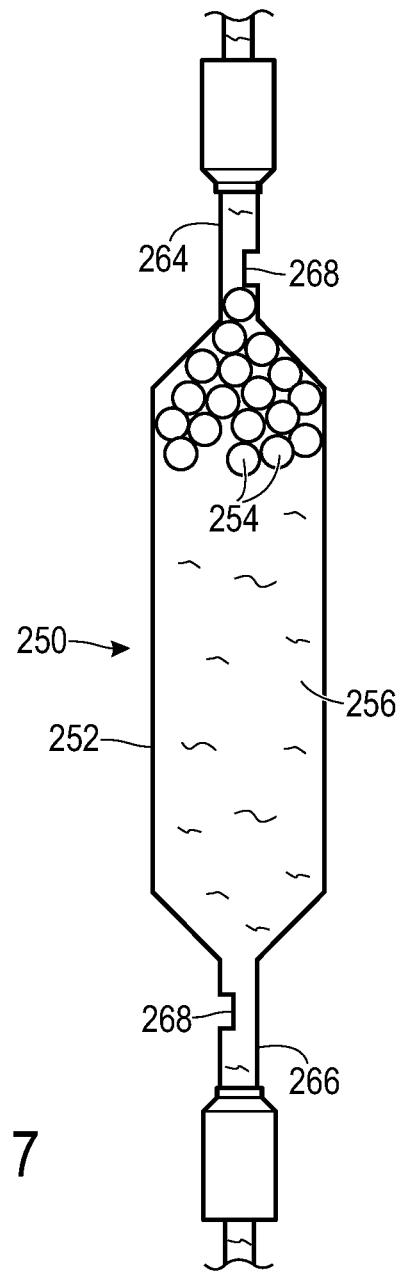
FIG. 7 is a side view of yet another exemplary reaction chamber holding an emulsion and having indented droplet-retention gates at opposite ends of the reaction chamber.

This example describes exemplary droplet-retention gates for reaction chambers; see FIGS. 6 and 7.

FIG. 6 shows selected aspects of an exemplary reaction control device 150, which is an embodiment of reaction control device 50 of Section II. Reaction control device 150 includes a reaction chamber 152 holding droplets 154 encapsulated by a carrier fluid 156. A pair of thermal zones 158a, 158b are located at opposite ends of the reaction chamber. Reaction chamber 152 has a curved inlet 164 and a curved outlet 166 each having a radial curvature forming a droplet-retention gate 168 shaped like a swan's neck. The curvature of inlet 164 and outlet 166 prevents droplets 154 from becoming trapped at either end of reaction chamber 152, such that substantially all of droplets 154 move as a group between thermal zones of reaction chamber 152 when the reaction chamber is properly reoriented.

FIG. 7 shows selected aspects of an exemplary reaction control device 250, which is an embodiment of reaction control device 50 of Section II. Reaction control device 250 includes a reaction chamber 252 holding droplets 254 encapsulated by a carrier fluid 256. Reaction chamber has an inlet 264 and an outlet 266 each having an indented droplet-retention gate 268. The width of droplet-retention gate 268 is less than the diameter of each droplet 254. Accordingly, droplets 254 do not pass through gate 268 when they migrate between thermal zones of the reaction chamber, but can be forced through gate 268 by a connected pump in order to enter and/or leave reaction chamber 252.

Example 2. Device and System Embodiments

This example describes exemplary device and system embodiments for controlling a chemical reaction in droplets; see FIGS. 8-11.

Figure 8:
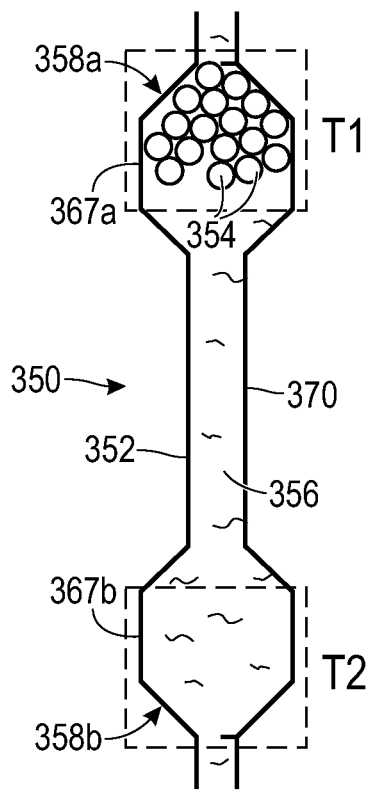
FIG. 8 is a schematic fragmentary illustration of selected aspects of an exemplary reaction control device holding an emulsion and including a reaction chamber having a pair of subchambers of greater diameter that are connected to one another via a channel of lesser diameter.

FIG. 8 shows selected aspects of an exemplary reaction control device 350, which is an embodiment of reaction control device 50 of Section II. Reaction control device 350 includes a reaction chamber 352 holding droplets 354 encapsulated by a carrier fluid 356. Reaction chamber 352 has a pair of thermal zones 358a, 358b maintained at different temperatures, T1 and T2, and located at opposite ends of the chamber. The extent of each thermal zone is indicated generally with a dashed box. Reaction chamber 352 forms a pair of wider subchambers 367a, 367b connected to one another via a narrower channel 370. Thermal zones 358a, 358b generally correspond to subchambers 367a, 367b, respectively.

Figure 9:
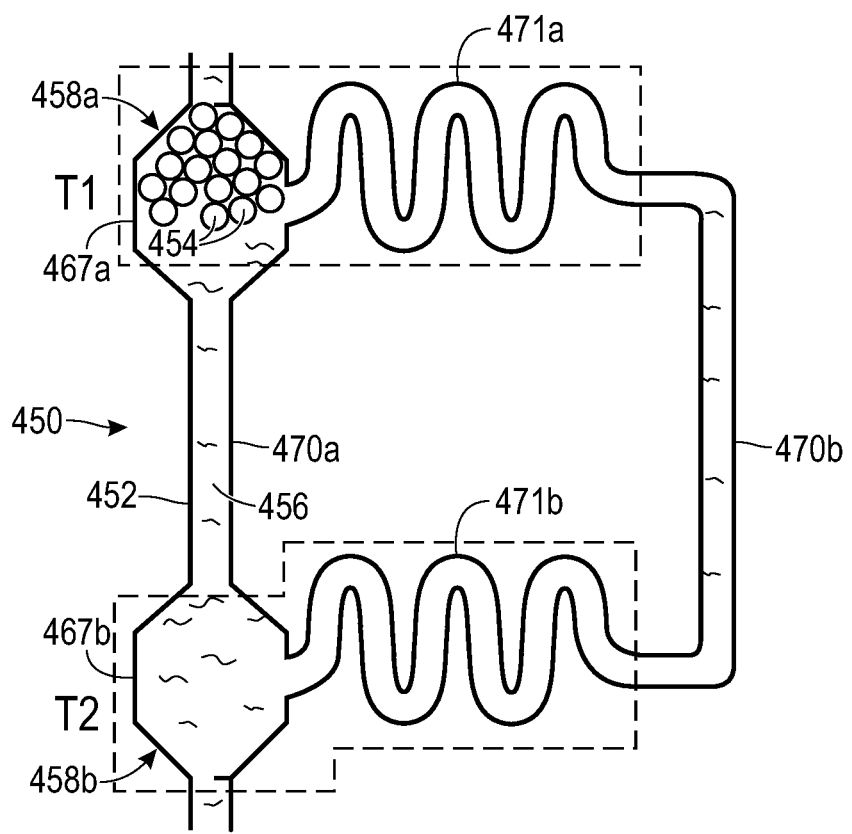
FIG. 9 is a schematic fragmentary illustration of selected aspects of an exemplary reaction control device holding an emulsion and including a reaction chamber having a pair of subchambers connected to one another via a droplet channel and a carrier fluid channel.

FIG. 9 shows selected aspects of an exemplary reaction control device 450, which is an embodiment of reaction control device 50 of Section II. Reaction control device 450 includes a reaction chamber 452 holding droplets 454 encapsulated by a carrier fluid 456. Reaction chamber 452 has a pair of thermal zones 458a, 458b maintained at different temperatures, T1 and T2, and located at opposite ends of the reaction chamber. The extent of each thermal zone is indicated generally with a dashed box. Reaction chamber 452 forms a pair of subchambers 467a, 467b connected to one another separately by a droplet channel 470a and a carrier fluid channel 470b. Carrier fluid channel 470b has a pair of meandering portions 471a, 471b attached to subchambers 467a, 467b, respectively. Reaction chamber 452 may be reoriented to move droplets 454 from subchamber 467a to subchamber 467b (or vice versa), predominantly or exclusively via droplet channel 470a. At the same time, a matching volume of carrier fluid 456 travels from subchamber 467b to subchamber 467a (or vice versa) via carrier fluid channel 470b. Each meandering portion 471a, 471b is located in the same thermal zone 458a or 458b as subchamber 467a or 467b. Accordingly, the matching volume of carrier fluid 456 that enters the subchamber is already preheated to the correct temperature, which helps to reduce temperature fluctuations in the subchambers and permits droplets 454 to reach each desired temperature more quickly.

Figure 10:
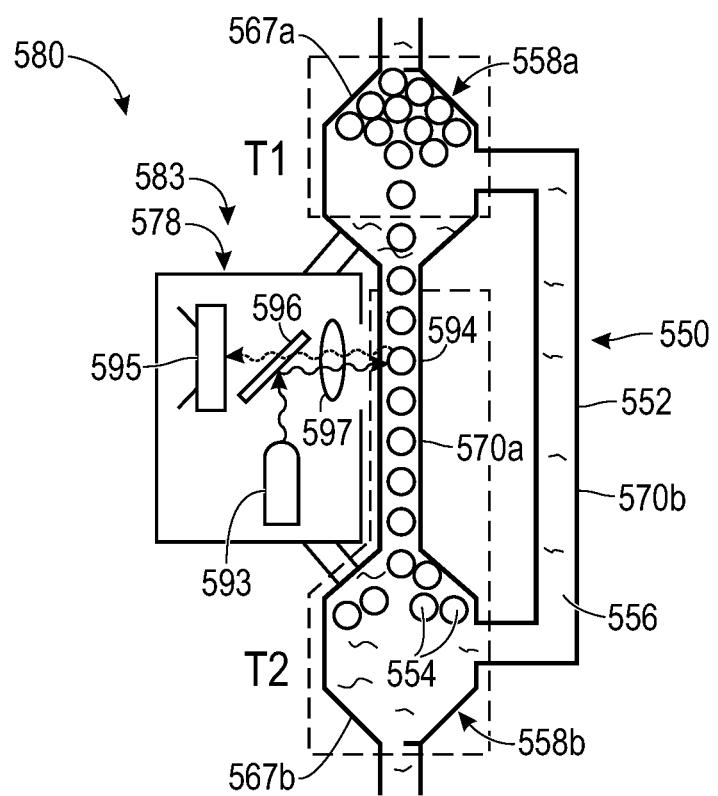
FIG. 10 is a schematic fragmentary illustration of selected aspects of an exemplary system for thermally controlling a chemical reaction and including a reaction control device optically coupled to a detection module.

FIG. 10 shows selected aspects of an exemplary system 580 for thermally controlling a chemical reaction in droplets. System 580 is an embodiment of system 80 of Section II and includes a reaction control device 550 optically coupled to a detection module 578. Reaction control device 550 includes a reaction chamber 552 holding droplets 554 encapsulated by a carrier fluid 556. Reaction chamber 552 has a pair of thermal zones 558a, 558b maintained at different temperatures, T1 and T2, and located at opposite ends of the chamber. The extent of each thermal zone is indicated generally with a dashed box. Reaction chamber 552 forms a pair of subchambers 567a, 567b connected to one another separately by a droplet channel 570a and a carrier fluid channel 570b.

A detection portion 583 of system 580 includes detection module 578 and a sensed zone 594 within droplet channel 570a that are optically coupled to one another. Detection module 578 is configured to detect light, such as photoluminescence, from droplets 554 as they travel along droplet channel 570a and through sensed zone 594 in response to reorientation of reaction chamber 552. The detection module 578 includes a light source 593, a photosensor 595, a beamsplitter 596, and an objective 597. Light source 593 generates optical radiation that propagates to sensed zone 594 via beamsplitter 596 and objective 597 and irradiates sensed zone 594. This irradiation may induce photoluminescence from a photoluminescent label in droplets 554. The photoluminescence is collected by objective 597, propagates through beamsplitter 596, and is incident on and detected by photosensor 595. Detection module 578 may, for example, be utilized to collect amplification data from droplets 554 during or after each of a plurality of thermal cycles to which the droplets are subjected in reaction chamber 552.

Figure 11:
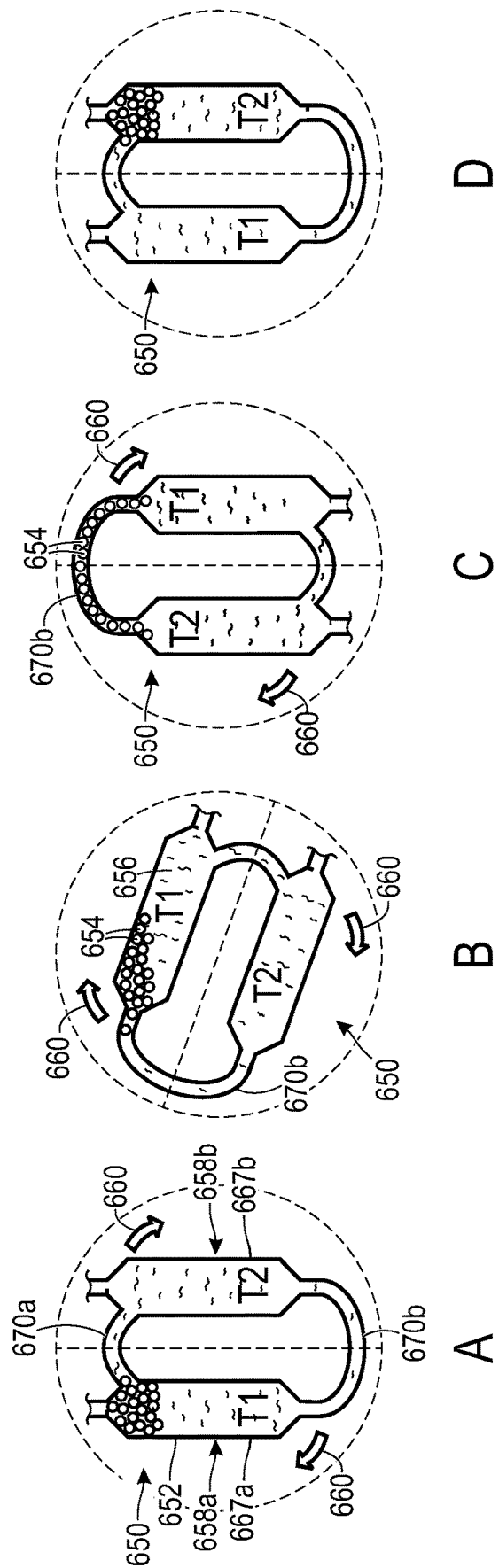
FIG. 11 is a schematic fragmentary illustration, in a series of panels (A-D), of an exemplary reaction control device holding an emulsion and including a reaction chamber having a pair of subchambers arranged laterally to one another and connected at opposite ends via a pair of channels, where the reaction chamber is being reoriented through a full turn in a plane of the pair of channels to move droplets of the emulsion between thermal zones of the reaction chamber.

FIG. 11 shows an exemplary reaction control device 650, which is an embodiment of reaction control device 50 of Section II. Reaction control device 650 includes a reaction chamber 652 holding droplets 654 encapsulated by a carrier fluid 656. Reaction chamber 652 has a pair of thermal zones 658a, 658b maintained at different temperatures, T1 and T2, and demarcated generally in dashed outline. Reaction chamber 652 includes a pair of subchambers 667a, 667b connected to one another via a pair of channels 670a, 670b. Panels A-D show reaction chamber 652 being reoriented through a full turn, indicated by turning arrows at 660, in a plane parallel to channels 670a, 670b, to move droplets 654 as a group from subchamber 667a to 667b. Droplets 654 can be returned to subchamber 667a by another full turn in the same or the opposite rotational direction.

Example 3. Thermal Zones Offset by Less than 180 Degrees

Figure 12:
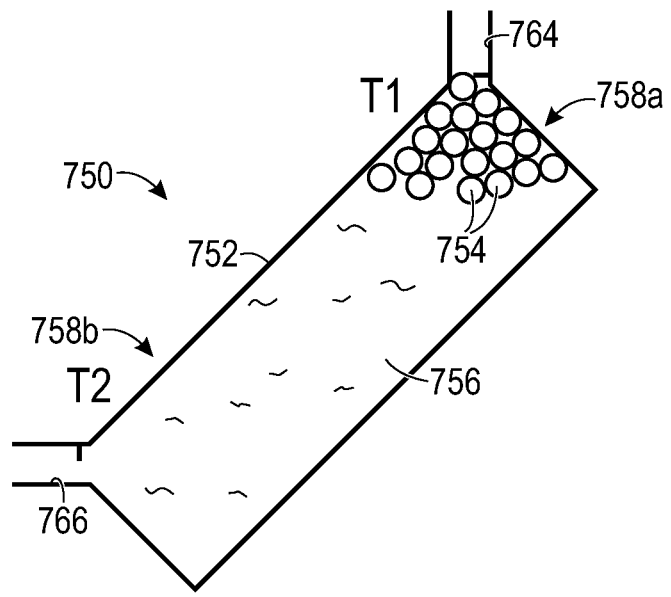
FIG. 12 is a schematic fragmentary illustration of selected aspects an exemplary reaction control device holding an emulsion and including a reaction chamber having a pair of thermal zones that are rotationally offset from one another by 90 degrees.
Figure 13:
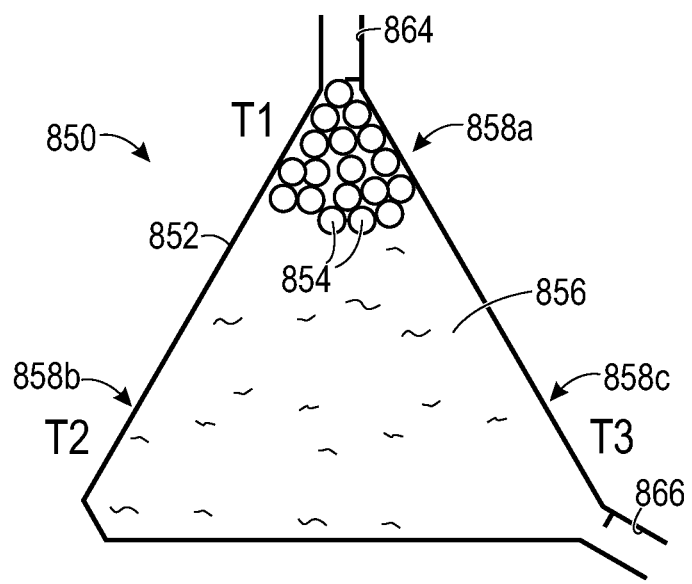
FIG. 13 is a schematic fragmentary illustration of selected aspects of an exemplary reaction control device holding an emulsion and including a reaction chamber having three thermal zones that are rotationally offset from one another by 120 degrees.

This example describes exemplary reaction control devices having thermal zones that are rotationally offset from one another by less than 180 degrees; see FIGS. 12 and 13.

FIG. 12 shows an exemplary reaction control device 750 including a rectangular reaction chamber 752 holding an emulsion of droplets 754 encapsulated by a carrier fluid 756. Reaction chamber 752 has a pair of thermal zones 758a, 758b that are rotationally offset from one another by 90 degrees in the plane of the image. In other words, rotating reaction chamber 752 by 90 degrees about an axis orthogonal to the plane of the image can move droplets 754 from thermal zone 758a to thermal zone 758b or vice versa. Accordingly, reaction chamber 752 may be configured to have up to four thermal zones each located generally at a different corner of the reaction chamber. An inlet 764 and an outlet 766 are in fluid communication with thermal zones 758a, 758b, respectively, but in other embodiments, one or both of the inlet and outlet may be placed instead at a different corner(s) of reaction chamber 752.

FIG. 13 shows an exemplary reaction control device 850 including a triangular reaction chamber 852 holding an emulsion of droplets 854 encapsulated by a carrier fluid 856. Reaction chamber 852 has three thermal zones 858a-c, at respective temperatures T1-T3, that are rotationally offset from one another by 120 degrees in the plane of the image. In other words, rotating reaction chamber 852 by 120 degrees about an axis orthogonal to the plane of the image can move droplets 854 from thermal zone 858a to either thermal zone 858b or thermal zone 858c. Droplets 854 can be moved to each of three thermal zones 858a-c in succession by rotating the reaction chamber one full turn or 120 degrees per thermal zone. An inlet 864 and an outlet 866 are in fluid communication with thermal zones 858a, 858b respectively, but in other embodiments, one or both of the inlet and outlet may be placed instead at a different corner(s) of reaction chamber 852. In other embodiments, the reaction chamber may have any suitable polygonal shape, such as a pentagon (having up to five thermal zones), a hexagon (up to six thermal zones), etc.

Example 4. Addition of Pre-Heated Carrier Fluid

This example describes an exemplary system 980 including reaction control device 150 of FIG. 6 and a pair of pumps, T1 pump 999a and T2 pump 999b, to drive preheated carrier fluid 156 into reaction chamber 152 holding droplets 154; see FIGS. 14 and 15.

System 980 has a pair of thermal zones 958a, 958b maintained at different temperatures T1 and T2. The thermal zones are demarcated generally by dashed boxes. Thermal zones 958a, 958b encompass thermal zones 158a, 158b of reaction chamber 152 and lengths of tubing 1001a, 1001b respectively connected to inlet 164 and outlet 166 of reaction chamber 152. Accordingly, lengths of tubing 1001a, 1001b serve as reservoirs holding preheated carrier fluid 156. In other embodiments, thermal zones 958a, 958b may encompass carrier fluid 156 held by chambers of pumps 999a, 999b and/or other chambers located along the flow paths intermediate pumps 999a, 999b and reaction chamber 152.

FIGS. 14 and 15 show reaction chamber 152 in a pair of configurations that are inverted relative to one another. In FIG. 14, droplets 154 have reached thermal zone 158a after migration from thermal zone 158b (in which the temperature is T2). To accelerate heating or cooling droplets 154 to temperature T1, a volume of carrier fluid 156 preheated to T1 is driven into reaction chamber 152 from length of tubing 1001a by the action of T1 pump 999a. This flow of carrier fluid 156 may be encouraged by T2 pump 999b, which may actively urge a corresponding volume of carrier fluid 156 out of reaction chamber 152 via outlet 166. Alternatively, T2 pump 999b may be replaced by a chamber that passively expands and contracts in response to the action of T1 pump 999a. In FIG. 15, droplets 154 have just reached thermal zone 158b in response to inverting reaction chamber 152 about a horizontal axis located in the plane of the image. To accelerate heating or cooling of droplets to T2, a volume of carrier fluid 156 preheated to T2 is driven into reaction chamber 152 from length of tubing 1001b by the action of T2 pump 999b. This flow of carrier fluid 156 may be encouraged by T1 pump 999a, which may actively urge a corresponding volume of carrier fluid 156 out of reaction chamber 152 via inlet 164.

Example 5. Centrifugation System to Drive Droplet Travel

This example describes a centrifugation system 1080 including a plurality of reaction control devices 1050a-d each having a thermally-zoned reaction chamber 1052 to hold sample-containing droplets (e.g., including Samples 1-4); see FIGS. 16-19. Centrifugation system 1080 is an embodiment of system 80 of FIG. 5.

To increase the thermal cycling rate, the droplets are moved more rapidly between the different thermal zones. This can be achieved by using a centrifuge to generate a g-force to drive the prospective droplet fluid first to one end. To drive it back to the other end, the reaction chamber is flipped over while spinning. However, system 1080 alternatively can be operated without centrifugation, by using gravity instead of a g-force to drive travel of droplets between thermal zones.

Figure 16:
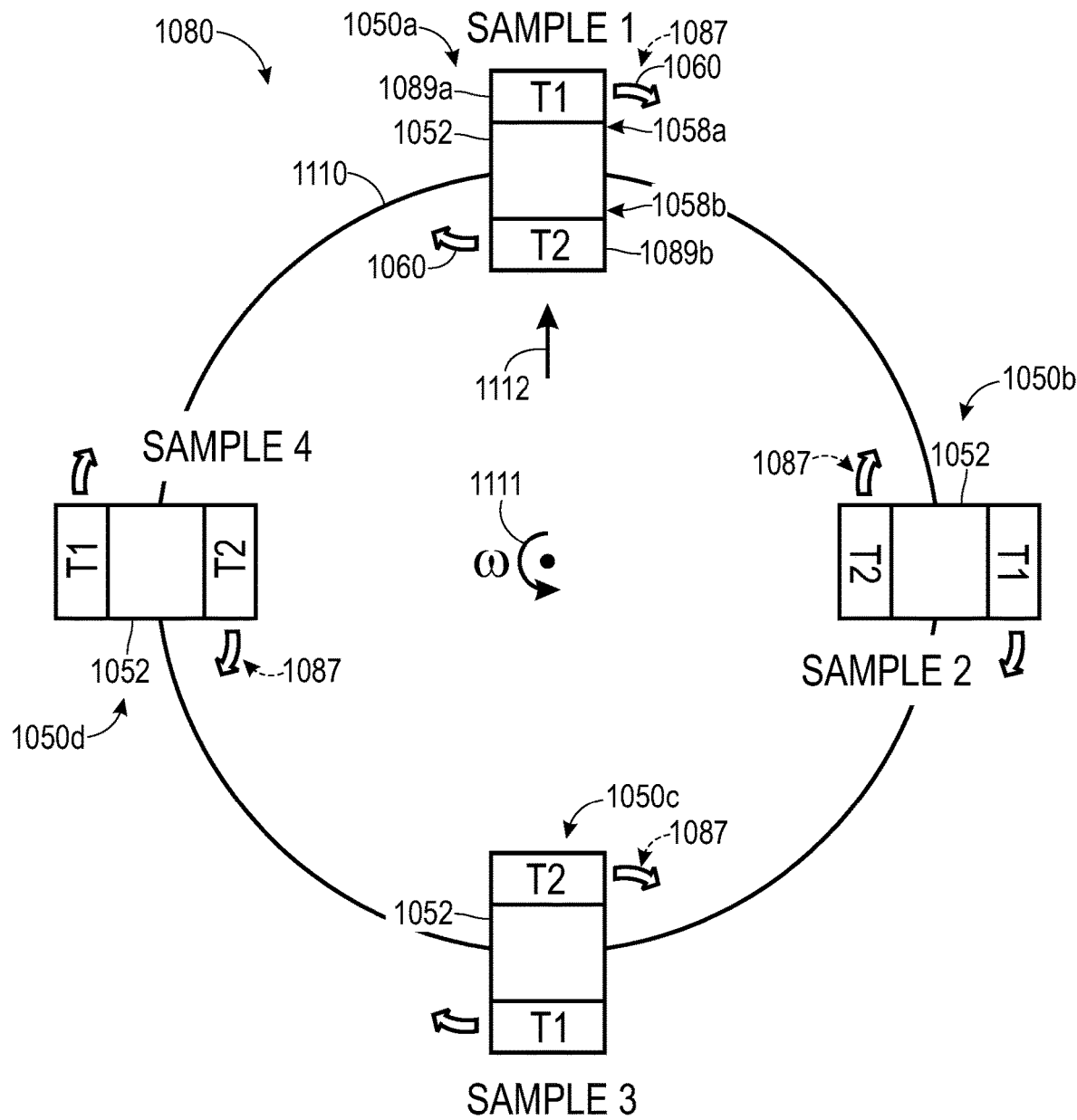
FIG. 16 is a schematic top plan view of an exemplary centrifugation system having a plurality of reaction control devices for thermally controlling a chemical reaction in droplets.

Reaction control devices 1050a-d are supported by a rotor 1110, which is rotated about an axis, indicated at 1111 (see FIG. 16). This rotation applies a g-force 1112 to an emulsion held by each reaction chamber 1052. (Only the g-force for reaction control device 1050a is shown in FIG. 16.) The g-force 1112 may be at least about 2, 5, 10, 25, 50, or 100 times the force of gravity, to move droplets more rapidly between thermal zones, relative to gravity-driven migration.

Figure 17:
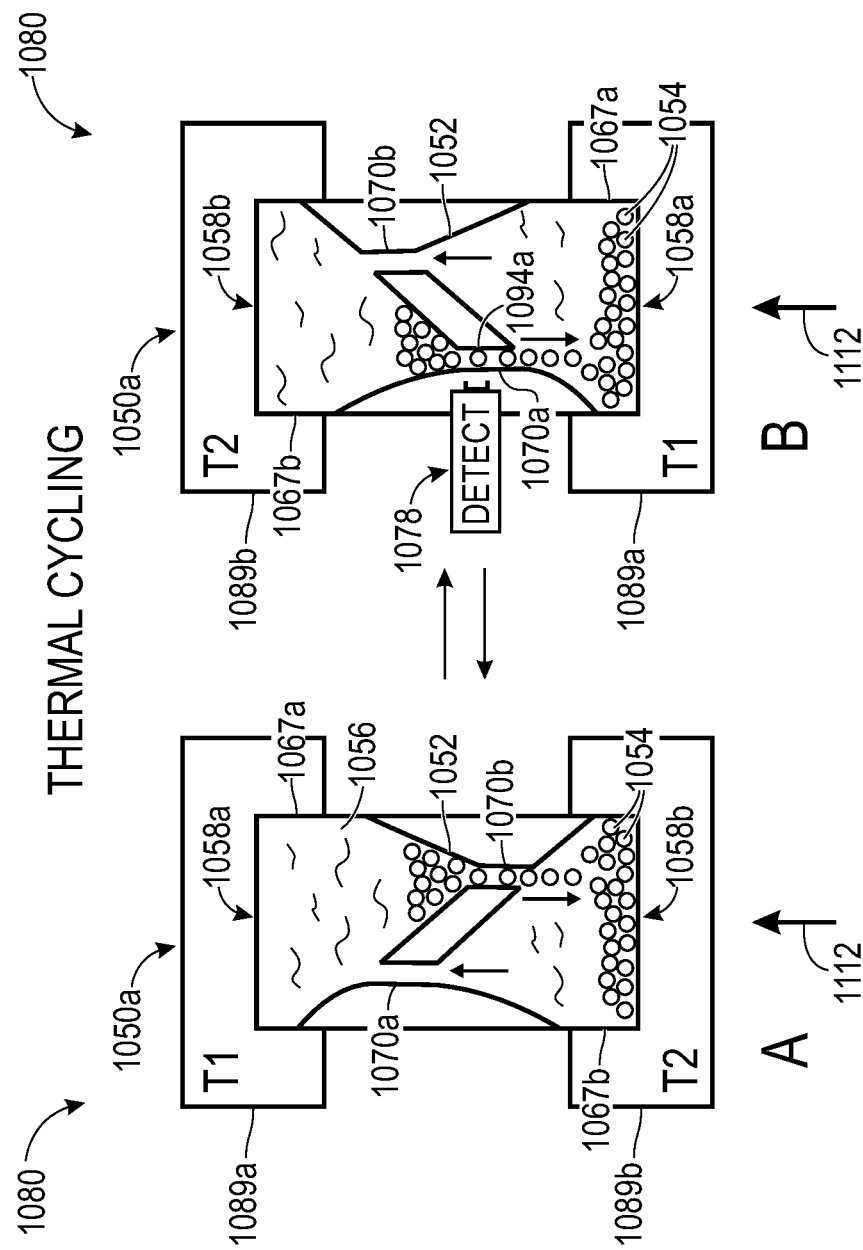
FIG. 17 is a schematic illustration of one of the reaction control devices of FIG. 16 being used for two-step thermal cycling of droplets to promote nucleic acid amplification in the droplets, with the reaction chamber of the reaction control device being inverted with respect to the centrifugal g-force between panels A and B.

Each reaction control device 1050a-d has a pair of heaters 1089a, 1089b to create thermal zones 1058a, 1058b of different temperature (e.g., T1 and T2 respectively) in each reaction chamber 1052 (see FIGS. 16 and 17). A respective orienting drive 1087 is operatively associated with each reaction control device 1050a-d (see FIG. 16). The orienting drive is configured to change the orientation of the reaction control device, indicated by turning arrows at 1060 for reaction control device 1050a, to move droplets between the pair of thermal zones while rotor 1110 is spinning. This change in orientation is with respect to the g-force 1112 exerted on the reaction control device. Each orienting drive 1087 may rotate the corresponding reaction control device 1050a-d by any suitable angle, such as flipping each device one-half turn in the depicted embodiment, about a respective rotation axis that is transverse or parallel to the rotation axis of rotor 1110. This reorientation of each reaction chamber 1052 moves droplets from one thermal zone 1058a or 1058b to the other thermal zone 1058b or 1058a.

FIG. 17 shows reaction control device 1050a of system 1080 being used for two-step thermal cycling to promote nucleic acid amplification in droplets (e.g., in only a subset of the droplets in chamber 1052 that contain a target sequence). An amplification signal may be detected from droplets 1054 during or after each thermal cycle of any suitable number of thermal cycles, such as every thermal cycle, as shown. Reaction chamber 1052 has a pair of channels 1070a, 1070b that separately connect a pair of subchambers 1067a, 1067b to one another. Subchamber 1067a may be maintained at temperature T1 and subchamber 1067b at temperature T2 by heaters 1089a, 1089b. During each thermal cycle, droplets 1054 migrate to thermal zone 1058a (temperature T1) and to thermal zone 1058b (temperature T2).

Panel A of FIG. 17 shows droplets 1054 in the process of migrating from subchamber 1067a (thermal zone 1058a at temperature T1) to subchamber 1067b (thermal zone 1058b at temperature T2) via channel 1070b. A matching volume of carrier fluid 1056 is moving in the opposite direction via channel 1070a.

Panel B of FIG. 17 shows reaction control device 1050a rotated one-half turn with respect to panel A (to change the orientation of reaction chamber 1052 relative to g-force 1112). Droplets 1054 are migrating from subchamber 1067b (thermal zone 1058b at temperature T2) to subchamber 1067a (thermal zone 1058a at temperature T1) via channel 1070a. In other words, droplets 1054 may migrate alternately via the two channels 1070a, 1070b (compare panels A and B). A detection module 1078 of system 1080 collects amplification data from droplets 1054 as each droplet passes through a sensed zone 1094a of channel 1070a. In other embodiments, reaction chamber 1052 may have only one channel connecting subchambers 1067a and 1067b to one another (e.g., see Section II). In other embodiments, reaction chamber 1052 may be configured such that droplets 1054 migrate back and forth between the thermal zones predominantly or exclusively via the same channel (of a pair of channels).

Figure 18:
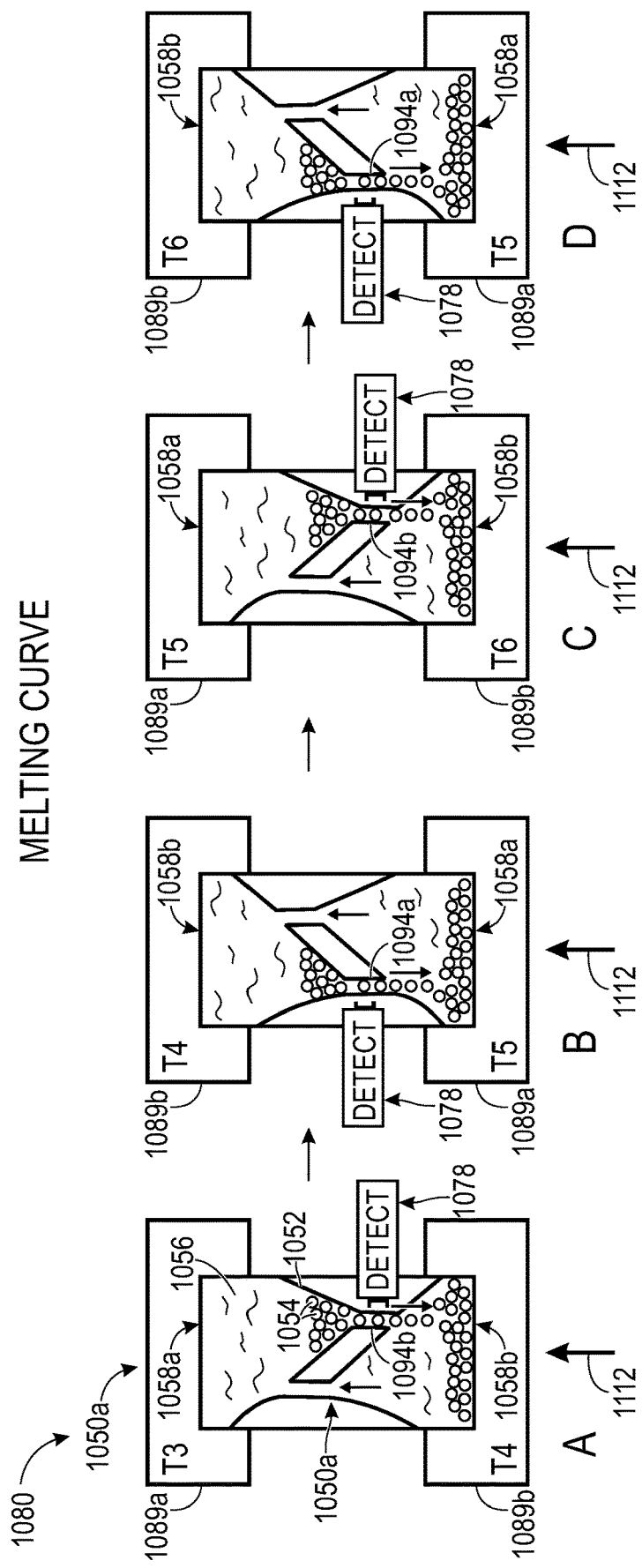
FIG. 18 is a schematic illustration of the reaction control device of FIG. 17 being used to generate a melting curve for amplification products in the droplets, by detecting an amplification signal at each of a series of different temperatures (shown in panels A-D).

FIG. 17 illustrates detection of an amplification signal at only one temperature. However, the amplification assay may be rendered more informative by detecting an amplification signal from droplets 1054 at two, three, or more different temperatures, to distinguish amplification products having different melting temperatures from one another. For example, panels A-D of FIG. 18 show reaction control device 1050a being used to generate a melting/annealing curve for amplification products in the droplets. An amplification signal is detected from the droplets passing alternately through sensed zones 1094a and 1094b using detection module 1078, in response to each inversion of reaction chamber 1052. The droplets have an increasing or decreasing series of different temperatures T3-T6 in panels A-D respectively (also see FIG. 3). Detection of the amplification signal may be performed before and/or after thermal cycling of the droplets has been completed. In panel A, droplets 1054 are passing through sensed zone 1094b from thermal zone 1058a at temperature T3 to thermal zone 1058b at temperature T4. In panel B, droplets 1054 are passing through sensed zone 1094a from thermal zone 1058b at temperature T4 to thermal zone 1058a, which is now at temperature T5. In panel C, droplets 1054 are passing through sensed zone 1094b from thermal zone 1058a at temperature T5 to thermal zone 1058b, which is now at temperature T6. In panel D, droplets 1054 are passing through sensed zone 1094a from thermal zone 1058a at temperature T6 to thermal zone 1058b (still at temperature T5).

Figure 19:
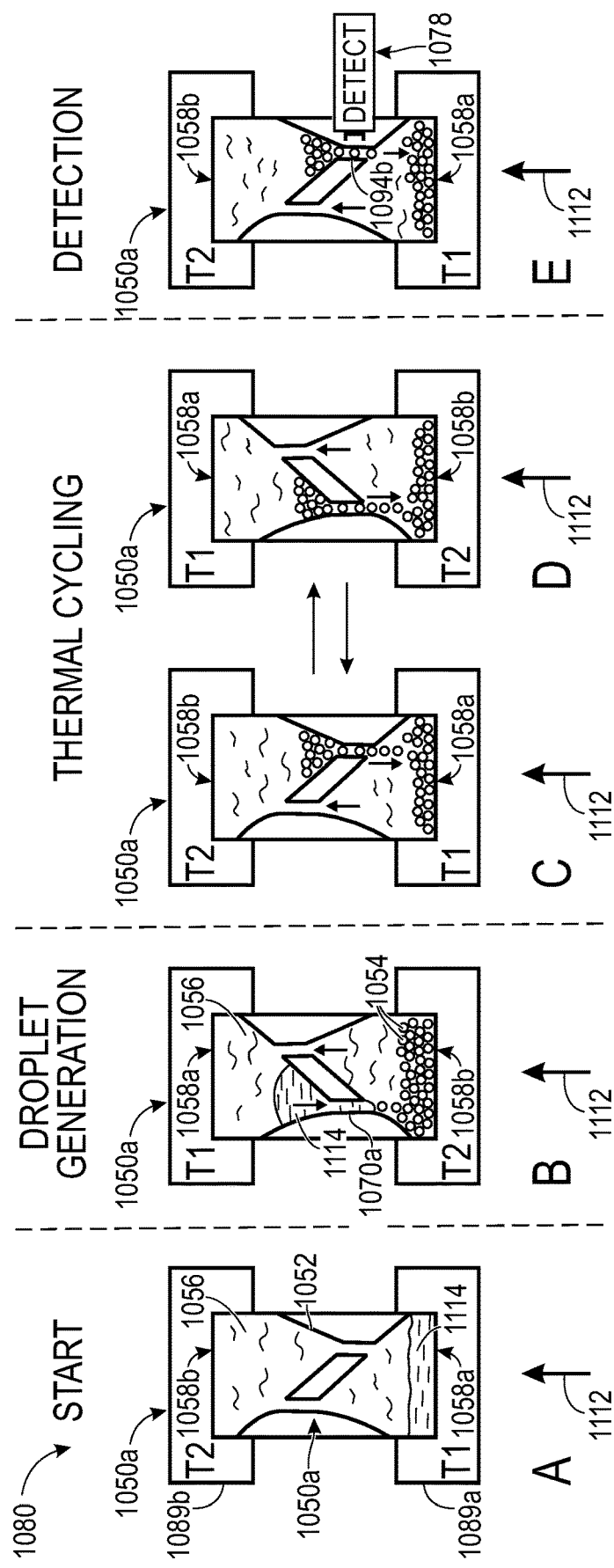
FIG. 19 is a schematic illustration of the reaction control device of FIG. 17 being used for droplet generation, thermal cycling of droplets, and detection of an amplification signal from the droplets after thermal cycling.

FIG. 19 shows reaction control device 1050a of FIG. 17 being used for droplet generation (panels A and B), thermally cycling droplets (panels C and D), and detection of an amplification signal from the droplets (panel E). In panel A, reaction chamber 1052 contains carrier fluid 1056 and a (non-partitioned) reaction mixture 1114 that are immiscible with one another. In panel B, reaction chamber 1052 has been flipped relative to panel A. In response, reaction mixture 1114 travels from thermal zone 1058a to thermal zone 1058b via channel 1070a. Reaction mixture 1114 is partitioned into droplets 1054 as the reaction mixture leaves the outlet of channel 1070a. In panels C and D, two-step thermal cycling is performed by flipping reaction chamber 1052 multiple times to move droplets 1054 back and forth between thermal zones 1058a and 1058b. In panel E, an amplification signal is detected by detection module 1078 from droplets 1054 passing through sensed zone 1094a.

Example 6. Flow-Through System for Thermal Control

Figure 20:
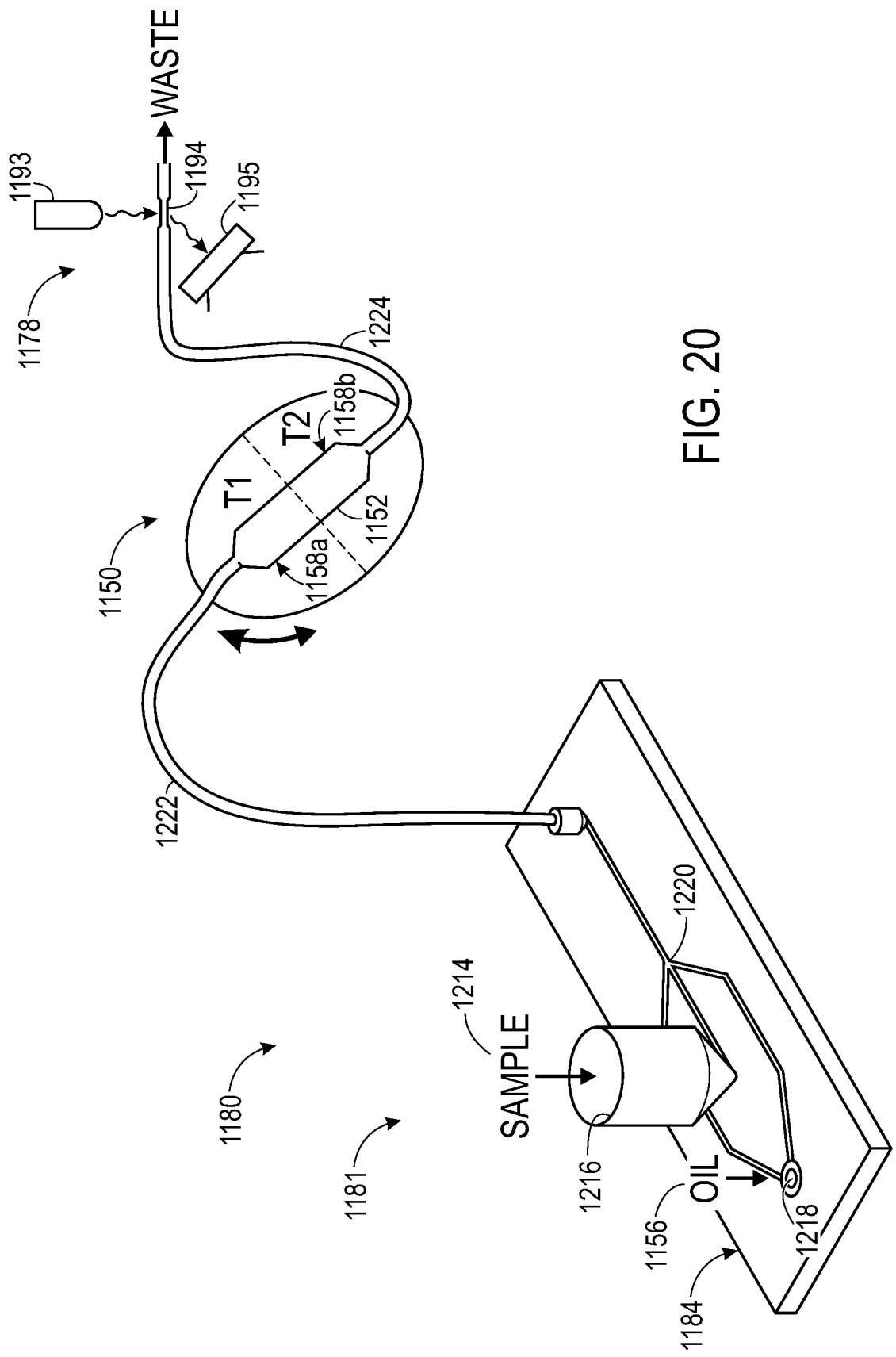
FIG. 20 is a schematic view of any exemplary flow-through system for thermally controlling a chemical reaction in droplets.

This example describes a flow-through system 1180 including an encapsulation assembly 1181, a reaction control device 1150, and a sensed zone 1194 arranged in series; see FIG. 20. Flow-through system 1180 is an embodiment of system 80 of FIG. 5.

Encapsulation assembly 1181 has a droplet generator 1184. The droplet generator receives a sample-containing reaction mixture 1214 via a sample inlet 1216 and carrier fluid 1156, such as oil, via a carrier inlet 1218. Reaction mixture 1214 and carrier fluid 1156 flow in different channels to a channel intersection 1220 at which an emulsion of droplets in carrier fluid 1156 is generated. The emulsion flows to reaction control device 1150 via an inflow channel 1222. Reaction control device 1150 has a reaction chamber 1152 including at least two thermal zones 1158a, 1158b. Droplets of the emulsion can be heated to different temperatures, such as thermally cycled, in reaction chamber 1152 by changing its orientation with respect to gravity as described elsewhere herein. Changing the orientation controls a chemical reaction, such as amplification of a target sequence in the droplets. The emulsion then flows out of reaction chamber 1152 via an outflow channel 1224 and passes through a sensed zone 1194 that is optically coupled to a detection module 1178. The detection module may have a light source 1193 to irradiate sensed zone 1194 and a photosensor 1195 to detect light from sensed zone 1194. The emulsion flows to waste downstream of sensed zone 1194.

IV. SELECTED ASPECTS

This section describes selected aspects of the present disclosure as a series of indexed paragraphs.

A1. A method of controlling a chemical reaction, the method comprising: (i) creating a first thermal zone and a second thermal zone in a reaction chamber, the first and second thermal zones having different temperatures from one another; (ii) holding an emulsion in the reaction chamber, the emulsion including droplets encapsulated by a carrier fluid and having a density mismatch with the carrier fluid, each of the droplets including one or more reactants for the chemical reaction; and (iii) changing an orientation of the reaction chamber to move the droplets from the first thermal zone to the second thermal zone, such that a rate of the chemical reaction changes in at least a subset of the droplets.

A2. The method of paragraph A1, wherein changing an orientation starts or speeds up the chemical reaction in the at least a subset of the droplets.

A3. The method of paragraph A1 or A2, further comprising reorienting the reaction chamber to return the droplets to the first thermal zone.

A4. The method of paragraph A3, further comprising changing a temperature of the first thermal zone while the droplets are located in the second thermal zone before reorienting.

A5. The method of paragraph A3 or A4, wherein reorienting changes the rate of the chemical reaction again in the at least a subset of the droplets.

A6. The method of paragraph A5, wherein reorienting slows or stops the chemical reaction in the at least a subset of the droplets.

A7. The method of any of paragraphs A3 to A6, wherein reorienting causes a plurality of the droplets to pass through a sensed zone within the reaction chamber, the method further comprising detecting a signal related to the chemical reaction from the plurality of droplets passing through the sensed zone.

A8. The method of paragraph A7, wherein detecting a signal includes detecting photoluminescence from the plurality of droplets.

A9. The method of any of paragraphs A1 to A8, wherein the reaction chamber has at least three thermal zones including the first thermal zone and the second thermal zone, wherein the at least three thermal zones are individually maintained at selected temperatures that are different from one another, the method further comprising turning the reaction chamber such that the droplets move from the first thermal zone to each of the other at least three thermal zones.

A10. The method of any of paragraphs A1 to A9, wherein the chemical reaction is catalyzed by an enzyme, and wherein the enzyme is present in only a subset of the droplets, optionally the enzyme has a Poisson distribution among the droplets.

A11. The method of paragraph A10, wherein the one or more reactants include a reactant having a photoluminescence that is changed by the chemical reaction, the method further comprising detecting the photoluminescence from a plurality of the droplets.

A12. The method of any of paragraphs A1 to A9, wherein changing an orientation encourages generation of an amplicon corresponding to a target sequence present in at least a subset of the droplets, and wherein, optionally, a reactant of the one or more reactants is an oligonucleotide that hybridizes with the amplicon or the target sequence at one or both of the different temperatures.

A13. The method of paragraph A12, wherein the oligonucleotide hybridizes with the amplicon or target sequence at only one of the different temperatures.

A14. The method of paragraph A12 or A13, wherein at least one of the droplets does not contain the target sequence.

A15. The method of any of paragraphs A12 to A14, wherein at least one of the droplets contains only one copy of the target sequence before changing an orientation.

A16. The method of any of paragraphs A12 to A15, wherein each of the droplets contains a polymerase, a ligase, and/or a reverse transcriptase.

A17. The method of any of paragraphs A12 to A16, wherein each of the droplets includes one or more mononucleotides as a reactant for the chemical reaction.

A18. The method of any of paragraphs A12 to A17, wherein the chemical reaction adds one or more nucleotides to the oligonucleotide.

A19. The method of any of paragraphs A1 to A9 and A11 to A18, further comprising performing an isothermal amplification reaction in at least a subset of the droplets while the droplets are located in the second thermal zone, wherein the isothermal amplification reaction includes the chemical reaction.

A20. The method of paragraph A19, further comprising reorienting the reaction chamber to move the droplets from the second thermal zone to the first thermal zone, to slow or stop the isothermal amplification reaction.

A21. The method of any of paragraphs A1 to A9 and A11 to A18, further comprising performing PCR including the chemical reaction in at least a subset of the droplets while the droplets remain in the reaction chamber.

A22. The method of paragraph A21, wherein performing PCR includes thermally cycling the droplets by reorienting the reaction chamber multiple times to move the droplets to each of the first and second thermal zones multiple times.

A23. The method of paragraph A22, further comprising collecting amplification data from the droplets while the droplets remain in the reaction chamber.

A24. The method of paragraph A23, wherein the amplification data is collected from a plurality of the droplets passing through a sensed zone within the reaction chamber.

A25. The method of paragraph A23 or A24, wherein collecting amplification data includes detecting photoluminescence from the plurality of droplets.

A26. The method of any of paragraphs A23 to A25, wherein thermally cycling includes subjecting the droplets to a plurality of thermal cycles, and wherein collecting amplification data includes collecting amplification data from at least a subset of the droplets during or after each thermal cycle of two or more of the plurality of thermal cycles, optionally after every thermal cycle of the plurality of thermal cycles.

A27. The method of any of paragraphs A23 to A26, wherein collecting amplification data includes collecting amplification data from at least a subset of the droplets at each temperature of an increasing or decreasing series of temperatures, and generating a melting curve or an annealing curve using the amplification data.

A28. The method of paragraph A27, further comprising changing a temperature of at least one of the first and second thermal zones between a pair of temperatures of the series of temperatures.

A29. The method of any of paragraphs A21 to A28, wherein the PCR is driven by two-step thermal cycling using the first and second thermal zones.

A30. The method of any of paragraphs A21 to A28, wherein the PCR is driven by subjecting the droplets to a series of thermal cycles, wherein the reaction chamber includes a third thermal zone having a selected temperature that is different from the first and second thermal zones, the method further comprising moving the droplets to each of the first, second, and third thermal zones in each thermal cycle.

A31. The method of any of paragraphs A19 to A30, wherein the droplets contain a probe having a label, the method further comprising detecting an amplification signal from the label.

A32. The method of paragraph A31, wherein each of the droplets includes a polymerase having an exonuclease activity to degrade copies of the probe during the isothermal amplification or PCR.

A33. The method of paragraph A31, wherein the probe is not degraded by the isothermal amplification or PCR.

A34. The method of any of paragraphs A18 to A33, wherein the droplets contain an intercalating dye, the method further comprising detecting an amplification signal from the intercalating dye.

A35. The method of paragraphs A18 to A34, wherein the isothermal amplification or PCR amplifies a target sequence or a complement thereof, and wherein only a subset of the droplets contain the target sequence.

A36. The method of any of paragraphs A1 to A35, wherein the first and second thermal zones are connected to one another via a channel, and wherein changing an orientation causes at least a subset of the droplets to move from the first thermal zone to the second thermal zone via the channel.

A37. The method of paragraph A36, wherein a pair of channels separately connect the first and second thermal zones to one another.

A38. The method of paragraph A37, wherein the pair of channels are a droplet channel and a carrier fluid channel, and wherein changing an orientation causes the droplets to travel between the first and second thermal zones predominantly or exclusively via the droplet channel.

A39. The method of paragraph 38, wherein the carrier fluid channel has a first end located in the first thermal zone and a second end located in the second thermal zone.

A40. The method of paragraph A39, wherein a first end portion of the carrier fluid channel adjacent the first end and/or a second portion of the carrier fluid channel adjacent the second end follows a meandering path.

A41. The method of any of paragraphs A1 to A40, further comprising forming the droplets outside the reaction chamber; and introducing the formed droplets into the reaction chamber.

A42. The method of any of paragraphs A1 to A40, further comprising forming the droplets inside the reaction chamber.

A43. The method of any of paragraphs A1 to A42, wherein each of the droplets has a lower density than the carrier fluid.

A44. The method of any of paragraphs A1 to A43, wherein each of the droplets has a higher density than the carrier fluid.

A45. The method of any of paragraphs A1 to A44, further comprising rotating the reaction chamber a plurality of full turns to produce alternating movement of the droplets as a group between the first and second thermal zones.

A46. The method of any of paragraphs A1 to A45, further comprising rotating the reaction chamber alternately in opposite rotational directions to produce alternating movement of the droplets as a group between the first and second thermal zones.

A47. The method of any of paragraphs A1 to A46, further comprising rotating the reaction chamber during a series of rotation intervals each inducing relocation of the droplets as a group from one of the first and second thermal zones to the other of the first and second thermal zones, and wherein rotating the reaction chamber also includes pausing rotation of the reaction chamber between successive rotation intervals of the series of rotation intervals.

A48. The method of paragraph A47, wherein rotating the reaction chamber includes pausing rotation of the container during a series of pause intervals of at least two different durations.

A49. The method of any of paragraphs A1 to A48, further comprising driving preheated carrier fluid into the reaction chamber at the second thermal zone using a pump when the droplets reach the second thermal zone from the first thermal zone.

A50. The method of paragraph A49, wherein the preheated carrier fluid is preheated to the temperature of the second thermal zone.

A51. The method of paragraph A49 or A50, further comprising reorienting the reaction chamber to move the droplets from the second thermal zone to the first thermal zone, and driving preheated carrier fluid into the reaction chamber at the first thermal zone using a pump when the droplets reach the first thermal zone from the second thermal zone.

A52. The method of paragraph A51, wherein the preheated carrier fluid driven into the first thermal zone is preheated to the temperature of the first thermal zone.

A53. The method of any of paragraphs A1 to A52, wherein changing an orientation is performed while the reaction chamber is spinning in centrifuge.

A54. The method of any of paragraphs A1 to A53, further comprising detecting a reaction signal from a plurality of the droplets.

A55. The method of paragraph A54, wherein detecting a reaction signal includes detecting the reaction signal from each droplet of the plurality of the droplets passing through a sensed zone of the reaction chamber.

A56. The method of paragraph A54 or A55, wherein detecting a reaction signal includes detecting an amplification signal from a plurality of droplets after each cycle of a plurality of thermal cycles.

A57. The method of any of paragraphs A54 to A56, wherein detecting a reaction signal includes detecting an amplification signal from a plurality of the droplets at each of a series of increasing or decreasing temperatures in the reaction chamber to produce a melting curve or an annealing curve.

A58. The method of any of paragraphs A1 to A57, wherein a first heating device and a second heating device remain associated with the first and second thermal zones, respectively, as the orientation of the reaction chamber is changed.

A59. The method of any of paragraphs A1 to A58, wherein changing an orientation moves the first thermal zone from an elevation higher than the second thermal zone to an elevation lower than the second thermal zone if the droplets are less dense than the carrier fluid, or vice versa if the droplets are more dense than the carrier fluid.

B1. A system for controlling a chemical reaction, the system comprising: (i) a reaction chamber to hold an emulsion including droplets encapsulated by a carrier fluid and having a density mismatch with the carrier fluid, each of the droplets containing one or more reactants for the chemical reaction; (ii) a thermal control system configured to create a first thermal zone and a second thermal zone having different temperatures from one another in the reaction chamber; and (iii) an orienting drive configured to change an orientation of the reaction chamber to move the droplets as a group between the first thermal zone and the second thermal zone.

B2. The system of paragraph B1, further comprising a droplet generator configured to generate the droplets, the droplet generator being connected or connectable to the reaction chamber such that the droplets travel from the droplet generator to the reaction chamber.

B3. The system of paragraph B1 or B2, further comprising a detection module configured to detect a reaction signal from a plurality of the droplets each located in a sensed zone within or downstream of the reaction chamber.

B4. The system of paragraph B3, wherein the sensed zone is a region of a channel, wherein the detection module includes a light source to irradiate each droplet of the plurality of droplets passing through the sensed zone, and a detector to detect light from the sensed zone.

The term "exemplary" as used in the present disclosure, means "illustrative" or "serving as an example." Similarly, the term "exemplify" means "to illustrate by giving an example." Neither term implies desirability or superiority.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

I claim:

1. A method of controlling a chemical reaction, the method comprising:
    creating a first thermal zone and a second thermal zone in a reaction chamber, the first and second thermal zones having different temperatures from one another;
    holding an emulsion in the reaction chamber, the emulsion including droplets encapsulated by a carrier fluid and having a density mismatch with the carrier fluid, each of the droplets including one or more reactants for the chemical reaction; and
    changing an orientation of the reaction chamber to move the droplets from the first thermal zone to the second thermal zone, such that a rate of the chemical reaction changes in at least a subset of the droplets;
    wherein changing an orientation encourages generation of an amplicon corresponding to a target sequence present in at least a subset of the droplets; and
    wherein by design at least one of the droplets does not contain the target sequence.

2. The method of claim 1, wherein changing an orientation starts or speeds up the chemical reaction in the at least a subset of the droplets.

3. The method of claim 1, further comprising reorienting the reaction chamber to return the droplets to the first thermal zone.

4. The method of claim 3, further comprising changing a temperature of the first thermal zone while the droplets are located in the second thermal zone before reorienting.

5. The method of claim 3, wherein reorienting changes the rate of the chemical reaction again in the at least a subset of the droplets.

6. The method of claim 5, wherein reorienting slows or stops the chemical reaction in the at least a subset of the droplets.

7. The method of claim 3, wherein reorienting causes a plurality of the droplets to pass through a sensed zone within the reaction chamber, the method further comprising detecting a signal related to the chemical reaction from the plurality of droplets passing through the sensed zone.

8. The method of claim 1, wherein the reaction chamber has at least three thermal zones including the first thermal zone and the second thermal zone, wherein the at least three thermal zones are individually maintained at selected temperatures that are different from one another, the method further comprising turning the reaction chamber such that the droplets move from the first thermal zone to each of the other at least three thermal zones.

9. The method of claim 1, wherein the chemical reaction is catalyzed by an enzyme, and wherein the enzyme is present in only a subset of the droplets.

10. The method of claim 1, wherein the one or more reactants include a reactant having a photoluminescence that is changed by the chemical reaction, the method further comprising detecting the photoluminescence from a plurality of the droplets.

11. The method of claim 1, wherein a reactant of the one or more reactants is an oligonucleotide that hybridizes with the amplicon and/or the target sequence at one or both of the different temperatures, and wherein the oligonucleotide hybridizes with the amplicon or target sequence at only one of the different temperatures.

12. The method of claim 1, wherein at least one of the droplets contains only one copy of the target sequence before changing an orientation.

13. The method of claim 1, further comprising performing PCR including the chemical reaction in at least a subset of the droplets while the droplets remain in the reaction chamber.

14. The method of claim 13, further comprising collecting amplification data from the droplets while the droplets remain in the reaction chamber.

15. A method of controlling a chemical reaction, the method comprising:
creating a first thermal zone and a second thermal zone in a reaction chamber, the first and second thermal zones having different temperatures from one another;
holding an emulsion in the reaction chamber, the emulsion including droplets encapsulated by a carrier fluid and having a density mismatch with the carrier fluid, each of the droplets including one or more reactants for the chemical reaction; and
changing an orientation of the reaction chamber to move the droplets from the first thermal zone to the second thermal zone, such that a rate of the chemical reaction changes in at least a subset of the droplets;
wherein the chemical reaction is catalyzed by an enzyme, and wherein the enzyme is present in only a subset of the droplets.

16. A method of controlling a chemical reaction, the method comprising:
creating a first thermal zone and a second thermal zone in a reaction chamber, the first and second thermal zones having different temperatures from one another;
holding an emulsion in the reaction chamber, the emulsion including droplets encapsulated by a carrier fluid and having a density mismatch with the carrier fluid, each of the droplets including one or more reactants for the chemical reaction;
changing an orientation of the reaction chamber to move the droplets from the first thermal zone to the second thermal zone, such that a rate of the chemical reaction changes in at least a subset of the droplets;
reorienting the reaction chamber to return the droplets to the first thermal zone; and
changing a temperature of the first thermal zone while the droplets are located in the second thermal zone before reorienting.

* * * * *